(12) United States Patent
Coe et al.

(10) Patent No.: US 9,428,512 B2
(45) Date of Patent: Aug. 30, 2016

(54) COMPOUNDS

(71) Applicant: GlaxoSmithKline LLC, Wilmington, DE (US)

(72) Inventors: Diane Mary Coe, Stevenage (GB); Stephen Allan Smith, Stevenage (GB)

(73) Assignee: GLAXOSMITHKLINE LLC, Wilmington, DE (US)

( * ) Notice: Subject to any disclaimer, the term of this patent is extended or adjusted under 35 U.S.C. 154(b) by 0 days.

(21) Appl. No.: 14/443,903

(22) PCT Filed: Nov. 18, 2013

(86) PCT No.: PCT/US2013/070469
§ 371 (c)(1),
(2) Date: May 19, 2015

(87) PCT Pub. No.: WO2014/081643
PCT Pub. Date: May 30, 2014

(65) Prior Publication Data
US 2015/0299204 A1    Oct. 22, 2015

Related U.S. Application Data

(60) Provisional application No. 61/728,380, filed on Nov. 20, 2012.

(51) Int. Cl.
*C07D 487/04* (2006.01)
*A61K 39/39* (2006.01)
*A61K 39/00* (2006.01)

(52) U.S. Cl.
CPC .............. *C07D 487/04* (2013.01); *A61K 39/39* (2013.01); *A61K 2039/55511* (2013.01)

(58) Field of Classification Search
CPC .................................................... C07D 487/04
See application file for complete search history.

(56) References Cited

U.S. PATENT DOCUMENTS

| | | | |
|---|---|---|---|
| 5,962,479 A | 10/1999 | Chen | |
| 6,376,501 B1 | 4/2002 | Isobe et al. | |
| 6,552,192 B1 | 4/2003 | Hanuset et al. | |
| 7,125,880 B1 | 10/2006 | Chen | |
| 7,390,890 B2 | 6/2008 | Furneaux et al. | |
| 7,642,350 B2 | 1/2010 | Pryde | |
| 7,977,344 B2 | 7/2011 | Lazarides et al. | |
| 8,067,413 B2 | 11/2011 | Bonnert et al. | |
| 8,067,426 B2 | 11/2011 | Biggadike et al. | |
| 8,563,717 B2 | 10/2013 | Bazin-Lee et al. | |
| 8,575,181 B2 | 11/2013 | Campos et al. | |
| 8,575,340 B2 | 11/2013 | Bazin-Lee et al. | |
| 8,703,754 B2 | 4/2014 | Gibbon et al. | |
| 8,765,772 B2 | 7/2014 | Biggadike et al. | |
| 8,802,684 B2 | 8/2014 | Bazin-Lee et al. | |
| 9,173,872 B2 | 11/2015 | Coe et al. | |
| 2001/0020030 A1 | 9/2001 | Stewart et al. | |
| 2002/0037886 A1 | 3/2002 | Andersson et al. | |
| 2003/0187261 A1 | 10/2003 | Havlicek et al. | |
| 2003/0191086 A1 | 10/2003 | Hanus et al. | |
| 2003/0220365 A1 | 11/2003 | Stewart et al. | |
| 2003/0236216 A1 | 12/2003 | Devos et al. | |
| 2004/0063658 A1 | 4/2004 | Roberts et al. | |
| 2005/0054590 A1 | 3/2005 | Averett | |
| 2006/0029642 A1 | 2/2006 | Miljkovic et al. | |
| 2006/0052403 A1 | 3/2006 | Isobe et al. | |

(Continued)

FOREIGN PATENT DOCUMENTS

| | | |
|---|---|---|
| EP | 0773023 A1 | 5/1997 |
| EP | 1043021 A1 | 7/1999 |

(Continued)

OTHER PUBLICATIONS

Pinedo et al. (2000).*
McMahon et al. (2000).*
U.S. Appl. No. 14/443,924 (Coe et al.), filed May 19, 2015.
U.S. Appl. No. 14/443,932 (Coe et al.), filed May 19, 2015.
Akira, S., Toll-like receptors: critical proteins linking innate and acquired immunity, Nat. Immuno. 2001; 2(8); 675-680.
Allergic Rhinitis-Prevention (http://www.webmd.com/allergies/tc/allergic-rhinitis-prevention); WebMD: Allergic Health Center; Jun. 30, 2011.

(Continued)

*Primary Examiner* — Paul V Ward
(74) *Attorney, Agent, or Firm* — Leah M. Octavio; Andrea V. Lockenour

(57) ABSTRACT

The present invention relates to compounds of formula (I) and salts thereof:

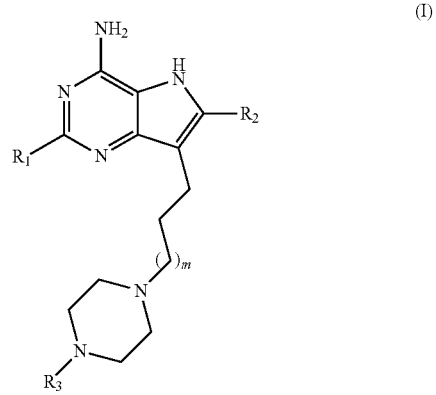

(I)

wherein $R_1$ is n-$C_{3-6}$alkyl; $R_2$ is hydrogen or methyl; $R_3$ is hydrogen or $C_{1-6}$alkyl, and m is an integer having a value of 1 to 4; are inducers of human interferon. Compounds which induce human interferon may be useful in the treatment of various disorders, for example the treatment of allergic diseases and other inflammatory conditions, for example allergic rhinitis and asthma, infectious diseases and cancer, and may also be useful as vaccine adjuvants.

14 Claims, No Drawings

(56) References Cited

U.S. PATENT DOCUMENTS

| | | |
|---|---|---|
| 2006/0148805 A1 | 7/2006 | Chen et al. |
| 2006/0264448 A1 | 11/2006 | Pryde |
| 2007/0190071 A1 | 8/2007 | Kurimoto et al. |
| 2007/0197478 A1 | 8/2007 | Jones et al. |
| 2007/0225303 A1 | 9/2007 | Ogita et al. |
| 2007/0275984 A1 | 11/2007 | Imogai et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0233948 A1 | 9/2009 | Evans et al. |
| 2009/0324551 A1 | 12/2009 | Carson et al. |
| 2009/0325877 A1 | 12/2009 | Grunt et al. |
| 2010/0010016 A1 | 1/2010 | Gangjee |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2011/0135671 A1 | 6/2011 | Bazin-Lee et al. |
| 2011/0229500 A1 | 9/2011 | Biggadike et al. |
| 2011/0269781 A1 | 11/2011 | Lazarides et al. |
| 2012/0035193 A1 | 2/2012 | Biggadike et al. |
| 2012/0135963 A1 | 5/2012 | Johnson |
| 2012/0171229 A1 | 7/2012 | Zepp et al. |
| 2012/0264768 A1 | 10/2012 | Gangee |
| 2012/0283438 A1 | 11/2012 | Lazarides et al. |
| 2012/0315291 A1 | 12/2012 | Basin-Lee et al. |
| 2014/0056928 A1 | 2/2014 | Coe et al. |
| 2014/0288099 A1 | 9/2014 | Ambery et al. |
| 2014/0336175 A1 | 11/2014 | Biggaike et al. |
| 2015/0225403 A1 | 8/2015 | Coe et al. |

FOREIGN PATENT DOCUMENTS

| | | |
|---|---|---|
| EP | 1348707 A1 | 10/2003 |
| EP | 1939198 A1 | 3/2007 |
| EP | 1939199 A1 | 7/2008 |
| EP | 2138497 A1 | 12/2009 |
| RU | 2221799 C2 | 1/2004 |
| WO | 9533750 A1 | 12/1995 |
| WO | WO-9749706 A1 | 12/1997 |
| WO | WO-99/40091 A1 | 8/1999 |
| WO | WO-00/43394 A1 | 7/2000 |
| WO | 0149688 A1 | 7/2001 |
| WO | 0183472 A1 | 11/2001 |
| WO | WO-03/053970 A1 | 7/2003 |
| WO | 2004018496 A1 | 3/2004 |
| WO | 2004029054 A1 | 4/2004 |
| WO | WO2004029054 A1 | 4/2004 |
| WO | 2005002520 A2 | 1/2005 |
| WO | 2005020892 A2 | 3/2005 |
| WO | 2005025583 A2 | 3/2005 |
| WO | 2005079195 A2 | 9/2005 |
| WO | 2005097800 A1 | 10/2005 |
| WO | WO-2005/110410 A2 | 11/2005 |
| WO | WO-2006/030031 A1 | 3/2006 |
| WO | 2006117670 A1 | 11/2006 |
| WO | 2007013964 A1 | 2/2007 |
| WO | 2007028129 A1 | 3/2007 |
| WO | 2007034881 A1 | 3/2007 |
| WO | WO-2007/024944 A1 | 3/2007 |
| WO | 2007041863 A1 | 4/2007 |
| WO | 2007093901 A1 | 8/2007 |
| WO | 2007110868 A1 | 10/2007 |
| WO | 2007138084 A1 | 12/2007 |
| WO | 2007142755 A2 | 12/2007 |
| WO | 2008004948 A1 | 1/2008 |
| WO | 2008101867 A1 | 8/2008 |
| WO | WO-2008/100457 A2 | 8/2008 |
| WO | 2008114008 A1 | 9/2008 |
| WO | WO-2008/154221 A2 | 12/2008 |
| WO | 2009019505 A1 | 2/2009 |
| WO | WO-2009/023179 A2 | 2/2009 |
| WO | 2009078798 A1 | 6/2009 |
| WO | WO-2010/006025 A1 | 1/2010 |
| WO | 2010018130 A1 | 2/2010 |
| WO | 2010018131 A1 | 2/2010 |
| WO | 2010018132 A1 | 2/2010 |
| WO | 2010018133 A1 | 2/2010 |
| WO | 2010018134 A1 | 2/2010 |
| WO | 2010083725 A1 | 7/2010 |
| WO | 2011017611 A1 | 2/2011 |
| WO | 2011098451 A1 | 8/2011 |
| WO | 2011098452 A1 | 8/2011 |
| WO | 2012009258 A2 | 1/2012 |
| WO | 2012106343 A2 | 8/2012 |
| WO | 2014081643 A1 | 5/2014 |
| WO | 2014081644 A1 | 5/2014 |
| WO | 2014081645 A1 | 5/2014 |
| WO | 2015124591 A1 | 8/2015 |

OTHER PUBLICATIONS

Asthma Prevention (http://www.webmd.com/asthma/guide/asthma-prevention); WebMD: Asthma Health Center; May 13, 2012.

Berge, S.M., et al. J. Pharmaceutical Science, Published 1977, vol. 66, pp. 1-19.

Borden E.C., et al., Interferons at age 50: past, current and future impact on biomedicine. Nat Rev. Drug Discov., Dec. 2007, 6(12), 975-990.

Czarniecki, M. Small Molecule Modulators of Toll-like Receptors, Nov. 13, 2008, vol. 51(21), 6621-6626.

Corren, J., et al.; A Randomized, Controlled, Phase 2 Study of AMG 317, an IL-4Rα Antagonist, in Patients with Asthma; Am. J. Respir. Crit. Care Med.; 2010; vol. 181; pp. 788-796.

Cryz, S.J. et al.; Immunotherapy and Vaccines; Ullmann's Encyclopedia of Industrial Chemistry; 2000; vol. 18; pp. 647-722.

Dermer, G.B. Another Anniversary for the War on Cancer, Bio/Technology, 1994, 12, 320.

Freshney, R.I., et al., "Culture of Animal Cells." A Manual of Basic Technique, Alan R. Liss, Inc., 1983, New York, 1-7.

Flood-Page, P. et al.; A Study to Evaluate Safety and Efficacy of Mepolizumab in Patients with Moderate Persistent Asthma; Am. J. Respir. Crit. Care Med.; Dec. 1, 2007; vol. 176, No. 11; pp. 1062-1071.

Gautschi, O., et al. "Aurora Kinases as Anticancer Drug Targets." Clin Cancer Res., Mar. 15, 2008, 14(6), 1639-1648.

Gauvreau, G.M. et al.; Effects of Interleukin-13 Blockade on Allergen-induced Airway Responses in Mild Atopic Asthma: Am. J. Respir. Crit. Care Med.; Nov. 5, 2010; doi:1 0.1164/rccm.201 008-121 OOC.

Golub, T.R., et al. "Molecular Classification of Cancer: Class Discovery and Class Prediction by Gene Expression Monitoring." Science, Oct. 15, 1999, 286, 531-537.

Gould P.L.; Salt Selection for Basic Drugs; International Journal of Pharmaceutics; 1986; 33; 201-217.

Haldar, P., et al., Mepolizumab and Exacerbations of Refractory Eosinophilic Asthma; The New England Journal of Medicine; 2009; vol. 360(10): pp. 973-984.

Hirota, K., et al.; "Discovery of 8-Hydroxyadenines as a Novel Type of Interferon Inducer"; J. Med. Chem.; 2002; vol. 45, No. 25; pp. 5419-5422; American Chemical Society.

Huber, J.P et al.; Cutting Edge: Type I IFN Reverses Human Th2 Commitment and Stability by Suppressing GATA3; The Journal of Immunology; 2010; vol. 185; pp. 813-817.

Hussein, W.M., et al. Toll-like receptor agonists: a patent review (2011-2013); Expert Opinion on Therapeutic Patents, Jan. 24, 2014, pp. 1-18.

(56) References Cited

OTHER PUBLICATIONS

Isobe, Y., et al.; Synthesis and Biological Evaluation of Novel 9-Substituted-8-hydroxyadenine Derivatives as Potent Interferon Inducers; J. Med. Chem.; 2006; vol. 49, No. 6; pp. 2088-2095; American Chemical Society.

Kariyawasam, H.H., Et al.; Effects of Anti-IL-13 (Novartis QAX576) on Inflammatory Responses Following Nasal Allergen Challenge (NAC); Am. J. Respir. Crit. Care Med.; 2009; vol. 179; A3642.

Kurimoto, A., et al.; Prodrugs of 9-Benzyl-8-hydroxy-2-(2-hydroxyethylthio)adenine: Potent Interferon Inducing Agents in Monkeys; Chem. Pharm. Bull.; 2004; vol. 52, No. 4; pp. 466-469; Pharmaceutical Society of Japan.

Leaker, B.R., et al. The Effects of the Novel Toll-Like Receptor 7 (TLR7) Agonist AZD 8848 on Allergen-Induced Responses in Patients With Mild Asthma, Publication p. A4184.

Liu, Y-J., IPC: Profesional Type 1 Interferon-Producing Cells and Plasmacytoid Dendridic Cell Precursors, Ann. Rev. Immunol., 2005; 23:275-306.

Ma, R., Additive effects of CpG ODN and R-848 as adjuvants on augmenting immune responses to HBsAg vaccination, Biochem. Biophys., Res. Commun., 2007; 361:537-542.

Mountzios, G., et al. "Aurora kinases as targets for cancer therapy." Cancer Treatment Reviews, 2008, 34, 175-182.

Pyne, S., et al. "Spingosine Kinase Inhibitors and Cancer: Seeking the Golden Sword of Hercules." Cancer Research, 2011, 71, 6576-6582.

Roemer, T., et al. "Auxiliary factors: a chink in the armor of MRSA resistance to β-lactam antibiotics." Current Opinion in Microbiology, 2013, 16, 538-548.

Simon, H-U., et al.; Clinical and immunological effects of low-dose IFN-α treatment in patients with corticosteroid-resistant asthma; Allergy; 2003; vol. 58; pp. 1250-1255.

Simone, J.V. Cecil Textbook of Medicine, edited by Bennet J.C. and Plum F., 20th edition, vol. 1, 1996, 1004-1010.

Snyder, J.W., et al. "Common bacteria whose susceptibility to antimicrobials is no longer predictable." J. Med. Liban, Pub Med Abstract, 2000, 48(4), 208-214.

Sugar, A.M., et al. "Comparison of Three Methods of Antifungal Susceptibility Testing with the Proposed NCCLS Standard Broth Microdilution Assay: Lack of Phenol Red." Diagno Microbiol Infect Dis, 1995, 21, 129-133.

Swarbrick, J., et al. Encyclopedia of Pharmaceutical Technology, Published 1996, vol. 13, pp. 453-499.

Tao, B., Treatment of allergic airway inflammation and hyper-responsiveness by imiquimod modulating transcription factors T-bet and GATA-3, Chin. Med. J. 2006; 119(8): 640-648.

Turner, W.W., et al. "Recent Advances in the Medicinal Chemistry of Antifungal Agents." Current Pharmaceutical Design, 1996, 2, 209-224.

\* cited by examiner

COMPOUNDS

This application is filed pursuant to 35 U.S.C. §371 as a United States National Phase Application of International Patent Application No. PCT/US2013/070469 filed Nov. 18, 2013, which claims priority from Provisional Application No. 61/728,380 filed Nov. 20, 2012.

TECHNICAL FIELD OF THE INVENTION

The present invention relates to compounds, processes for their preparation, compositions containing them, to their use in the treatment of various disorders in particular allergic diseases and other inflammatory conditions for example allergic rhinitis and asthma, infectious diseases, and cancer, and as vaccine adjuvants.

BACKGROUND OF THE INVENTION

Vertebrates are constantly threatened by the invasion of microorganisms and have evolved mechanisms of immune defence to eliminate infective pathogens. In mammals, this immune system comprises two branches; innate immunity and acquired immunity. The first line of host defence is the innate immune system, which is mediated by macrophages and dendritic cells. Acquired immunity involves the elimination of pathogens at the late stages of infection and also enables the generation of immunological memory. Acquired immunity is highly specific, due to the vast repertoire of lymphocytes with antigen-specific receptors that have undergone gene rearrangement.

Central to the generation of an effective innate immune response in mammals are mechanisms which bring about the induction of interferons and other cytokines which act upon cells to induce a number of effects. In man, the type I interferons are a family of related proteins encoded by genes on chromosome 9 and encoding at least 13 isoforms of interferon alpha (IFNα) and one isoform of interferon beta (IFNβ). Interferon was first described as a substance which could protect cells from viral infection (Isaacs & Lindemann, *J. Virus Interference. Proc. R. Soc. Lon. Ser. B. Biol. Sci.* 1957: 147, 258-267). Recombinant IFNα was the first approved biological therapeutic and has become an important therapy in viral infections and in cancer. As well as direct antiviral activity on cells, interferons are known to be potent modulators of the immune response, acting on cells of the immune system (Gonzalez-Navajas J. M. et al *Nature Reviews Immunology,* 2012; 2, 125-35).

Toll-like receptors (TLRs) are a family of ten Pattern Recognition Receptors described in man (Gay, N. J. et al, *Annu. Rev. Biochem.,* 2007: 46, 141-165). TLRs are expressed predominantly by innate immune cells where their rôle is to monitor the environment for signs of infection and, on activation, mobilise defence mechanisms aimed at the elimination of invading pathogens. The early innate immune-responses triggered by TLRs limit the spread of infection, while the pro-inflammatory cytokines and chemokines that they induce lead to recruitment and activation of antigen presenting cells, B cells, and T cells. The TLRs can modulate the nature of the adaptive immune-responses to give appropriate protection via dendritic cell-activation and cytokine release (Akira S. et al, *Nat. Immunol.,* 2001: 2, 675-680). The profile of the response seen from different TLR agonists depends on the cell type activated.

TLR7 is a member of the subgroup of TLRs (TLRs 3, 7, 8, and 9), localised in the endosomal compartment of cells which have become specialised to detect non-self nucleic acids. TLR7 plays a key rôle in anti-viral defence via the recognition of ssRNA (Diebold S. S. et al, *Science,* 2004: 303, 1529-1531; and Lund J. M. et al, *PNAS,* 2004: 101, 5598-5603). TLR7 has a restricted expression-profile in man and is expressed predominantly by B cells and plasmacytoid dendritic cells (pDC), and to a lesser extent by monocytes. Plasmacytoid DCs are a unique population of lymphoid-derived dendritic cells (0.2-0.8% of Peripheral Blood Mononuclear Cells (PBMCs)) which are the primary type I interferon-producing cells secreting high levels of interferon-alpha (IFNα) and interferon-beta (IFNβ) in response to viral infections (Liu Y-J, *Annu. Rev. Immunol.,* 2005: 23, 275-306).

Administration of a small molecule compound which could stimulate the innate immune response, including the activation of type I interferons and other cytokines via Toll-like receptors, could become an important strategy for the treatment or prevention of human diseases. Small molecule agonists of TLR7 have been described which can induce interferon alpha in animals and in man (Takeda K et al, *Annu. Rev. Immunol.,* 2003: 21, 335-76). TLR7 agonists include imidazoquinoline compounds such as imiquimod and resiquimod, oxoadenine analogues and also nucleoside analogues such as loxoribine and 7-thia-8-oxoguanosine which have long been known to induce interferon alpha (Czarniecki. M., *J. Med. Chem.,* 2008: 51, 6621-6626; Hedayat M. et al, *Medicinal Research Reviews,* 2012: 32, 294-325). This type of immunomodulatory strategy has the potential to identify compounds which may be useful in the treatment of allergic diseases (Moisan J. et al, *Am. J. Physiol. Lung Cell Mol. Physiol.,* 2006: 290, L987-995), viral infections (Horcroft N. J. et al, *J. Antimicrob. Chemther,* 2012: 67, 789-801), cancer (Krieg A., *Curr. Oncol. Rep.,* 2004: 6(2), 88-95), other inflammatory conditions such as irritable bowel disease (Rakoff-Nahoum S., *Cell.,* 2004, 23, 118(2): 229-41), and as vaccine adjuvants (Persing et al. *Trends Microbiol.* 2002: 10(10 Suppl), S32-7).

More specifically, allergic diseases are associated with a Th2-biased immune-response to allergens. Th2 responses are associated with raised levels of IgE, which, via its effects on mast cells, promotes a hypersensitivity to allergens, resulting in the symptoms seen, for example, in asthma and allergic rhinitis. In healthy individuals the immune-response to allergens is more balanced with a mixed Th2/Th1 and regulatory T cell response. TLR7 ligands have been shown to reduce Th2 cytokine and enhance Th1 cytokine release in vitro and to ameliorate Th2-type inflammatory responses in allergic lung models in vivo (Duechs M. J., *Pulmonary Pharmacology & Therapeutics,* 2011: 24, 203-214; Fili L. et al, *J. All. Clin. Immunol.,* 2006: 118, 511-517; Tao et al, Chin. Med. 1, 2006: 119, 640-648; Van L. P. *Eur. J. Immunol.,* 2011: 41, 1992-1999). Thus TLR7 ligands have the potential to rebalance the immune-response seen in allergic individuals and lead to disease modification. Recent clinical studies with the TLR7 agonist have shown repeated intranasal stimulation of TLR7 to produce a sustained reduction in the responsiveness to allergen in patients with both allergic rhinitis and allergic asthma (Greiff L. *Respiratory Research,* 2012: 13, 53; Leaker B. R. et al, *Am. J. Respir. Crit. Care Med.,* 2012: 185, A4184).

In the search for novel small molecule inducers of human interferon IFNα an assay strategy has been developed to characterise small molecule (regardless of mechanism) which is based on stimulation of primary human donor cells or whole blood with compounds, and is disclosed herein.

SUMMARY OF THE INVENTION

In a first aspect, the present invention is directed to compounds of formula (I) and salts thereof:

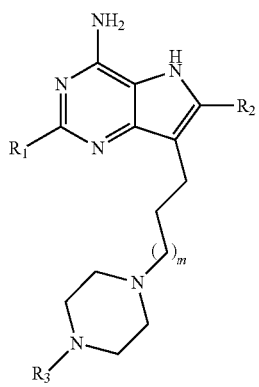

wherein:

$R_1$ is n-$C_{3-6}$alkyl;

$R_2$ is hydrogen or methyl;

$R_3$ is hydrogen or $C_{1-6}$alkyl;

m is an integer having a value of 1 to 4.

Certain compounds of the invention have been shown to be inducers of human interferon and may possess a desirable developability profile compared to known inducers of human interferon. In addition, certain compounds of the invention may also show selectivity for IFNα with respect to TNFα. Compounds which induce human interferon may be useful in the treatment of various disorders, for example the treatment of allergic diseases and other inflammatory conditions, for example allergic rhinitis and asthma, the treatment of infectious diseases and cancer. Accordingly, the invention is further directed to pharmaceutical compositions comprising a compound of formula (I), or a pharmaceutically acceptable salt thereof. The present invention is further directed to methods of treatments of disorders associated therewith using a compound of formula (I) or a pharmaceutically acceptable salt thereof, or a pharmaceutical composition comprising a compound of formula (I) or a pharmaceutically acceptable salt thereof.

The compounds of the invention may also have use as vaccine adjuvants. Consequently, the present invention is further directed to a vaccine composition comprising a compound of formula (I), or a pharmaceutically acceptable salt thereof, and an antigen or antigen composition.

Certain compounds of the invention are potent immunomodulators and accordingly, care should be exercised in their handling.

DETAILED DESCRIPTION OF THE INVENTION

In a first aspect, the present invention is directed to compounds of formula (I) and salts thereof:

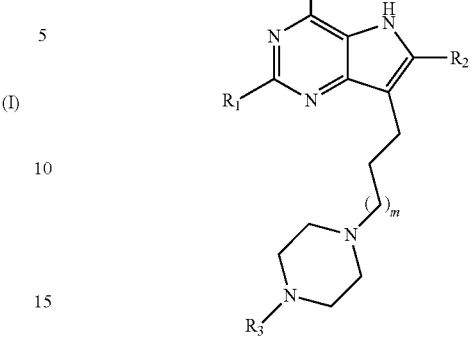

wherein:

$R_1$ is n-$C_{3-6}$alkyl;

$R_2$ is hydrogen or methyl;

$R_3$ is hydrogen or $C_{1-6}$alkyl;

m is an integer having a value of 1 to 4.

In a further aspect, $R_1$ is n-butyl.

In a further aspect, $R_2$ is hydrogen.

In a further aspect, $R_2$ is methyl.

In a further aspect, m is an integer having a value of 1, 2, 3, or 4.

In a further aspect, m is an integer having a value of 1 or 3.

In a further aspect, $R_3$ is isopropyl or ethyl.

Examples of compounds of formula (I) are provided in the following group, and form a further aspect of the invention:

2-Butyl-7-(5-(piperazin-1-yl)pentyl)-5H-pyrrolo[3,2-d]pyrimidin-4-amine,

2-Butyl-7-(5-(4-isopropylpiperazin-1-yl)pentyl)-5H-pyrrolo[3,2-d]pyrimidin-4-amine, 2-Butyl-7-(5-(4-isopropylpiperazin-1-yl)pentyl)-6-methyl-5H-pyrrolo[3,2-d]pyrimidin-4-amine, 2-Butyl-7-(5-(4-ethylpiperazin-1-yl)pentyl)-6-methyl-5H-pyrrolo[3,2-d]pyrimidin-4-amine, 2-Butyl-7-(3-(piperazin-1-yl)propyl)-5H-pyrrolo[3,2-d]pyrimidin-4-amine, 2-Butyl-7-(4-(4-isopropylpiperazin-1-yl)butyl)-5H-pyrrolo[3,2-d]pyrimidin-4-amine, and 2-Butyl-7-(3-(4-ethylpiperazin-1-yl)propyl)-5H-pyrrolo[3,2-d]pyrimidin-4-amine; and salts thereof.

As used herein, the term "alkyl" refers to a saturated, hydrocarbon chain having the specified number of member atoms. Unless otherwise stated, the term 'alkyl' includes straight and branched alkyl groups. For example, $C_{1-6}$alkyl refers to a saturated, straight or branched hydrocarbon chain having from 1 to 6 carbon atoms, such as ethyl and isopropyl, and n-$C_{3-6}$alkyl refers to a saturated, straight hydrocarbon chain having from 3 to 6 carbon atoms, such as n-propyl, and n-butyl.

It is to be understood that references herein to compounds of the invention mean a compound of formula (I) as the free base, or as a salt, for example a pharmaceutically acceptable salt.

In one aspect of the invention, a compound of formula (I) is in the form of a free base.

Salts of the compounds of formula (I) include pharmaceutically acceptable salts and salts which may not be pharmaceutically acceptable but may be useful in the preparation of compounds of formula (I) and pharmaceutically acceptable salts thereof. In one aspect of the invention, a compound of formula (I) is in the form of a pharmaceutically acceptable salt. Salts may be derived from certain inorganic or organic acids.

Examples of salts are pharmaceutically acceptable salts. Pharmaceutically acceptable salts include acid addition salts. For a review on suitable salts see Berge et al., *J. Pharm. Sci.*, 66:1-19 (1977).

Examples of pharmaceutically acceptable acid addition salts of a compound of formula (I) include inorganic acids such as, for example, hydrochloric acid, hydrobromic acid, orthophosphoric acid, nitric acid, phosphoric acid, or sulphuric acid, or with organic acids such as, for example, methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesuphonic, hexanoic acid or acetylsalicylic acid.

The invention includes within its scope all possible stoichiometric and non-stoichiometric forms of the salts of the compounds of formula (I). For example, a dimaleate or hemi-succinate salt of the compound of formula (I).

Salts may be formed using techniques well-known in the art, for example by precipitation from solution followed by filtration, or by evaporation of the solvent.

Typically, a pharmaceutically acceptable acid addition salt can be formed by reaction of a compound of formula (I) with a suitable acid (such as hydrobromic, hydrochloric, sulphuric, maleic, p-toluenesulphonic, methanesulphonic, naphthalenesulphonic or succinic acids), optionally in a suitable solvent such as an organic solvent, to give the salt which is usually isolated for example by crystallisation and filtration.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Solvates of the compounds of formula (I) are within the scope of the invention. As used herein, the term solvate encompasses solvates of both a free base compound as well as any salt thereof.

Certain of the compounds of the invention may contain chiral atoms and/or multiple bonds, and hence may exist in one or more stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

Certain of the compounds of the invention may exist in tautomeric forms. It will be understood that the present invention encompasses all of the tautomers of the compounds of the invention whether as individual tautomers or as mixtures thereof.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

The present invention also includes all suitable isotopic variations of a compound of formula (I) or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^2$H, $^3$H, $^{13}$C, $^{14}$C, $^{15}$N, $^{17}$O, $^{18}$O, $^{18}$F and $^{36}$Cl, respectively. Certain isotopic variations of a compound of formula (I) or a salt or solvate thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

It will be appreciated from the foregoing that included within the scope of the invention are solvates, hydrates, isomers and polymorphic forms of the compounds of formula (I) and salts and solvates thereof.

Compound Preparation

The compounds of formula (I) and salts thereof may be prepared by the methodology described hereinafter, constituting further aspects of this invention.

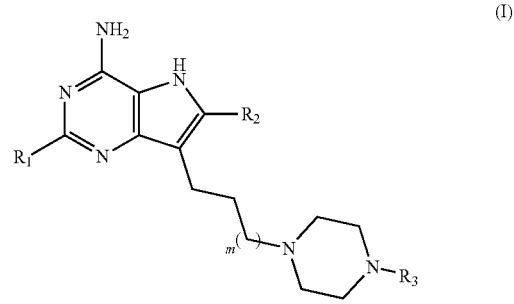

(I)

The compounds of formula (I) and salts thereof may be prepared by the methodology described hereinafter, constituting further aspects of this invention.

Accordingly, there is provided a process for the preparation of a compound of formula (I), which process comprises the deprotection of a compound of formula (II):

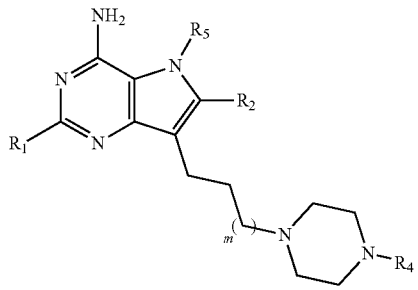

(II)

wherein $R_1$, $R_2$, and m are as defined hereinbefore for a compound of formula (I), $R_4$ is $R_3$ or is a suitable protecting group, such as, for example, t-butoxycarbonyl (BOC), $R_5$ is a protecting group, such as, for example, benzyloxymethyl (BOM), 2-(trimethylsilyl)ethoxymethyl or p-toluenesufonyl, and thereafter, if required, preparing a salt of the compound so-formed.

For example, a compound of formula (II) wherein $R_5$ is equivalent to BOM is dissolved in a suitable solvent, for example methanol or ethanol, and passed over a suitable catalyst, for example 10% palladium on carbon in the presence of hydrogen, at a suitable temperature, for example 20-60° C., in an apparatus such as the Thales H-cube™. The product (I) is isolated by removal of the solvent and purification if required.

For example, a compound of formula (II) wherein $R_4$ is BOC is dissolved in a suitable solvent, for example methanol, and treated with a solution of hydrogen chloride in a suitable solvent, for example 1,4-dioxane, at ambient temperature for a suitable period of time, for example 21 hours to give a compound of formula (II) where $R_4$=H which on removal of $R_5$ as above would give a compound of formula (I) where $R_3$=H.

A compound of formula (II) may be prepared by reaction of a compound of formula (III):

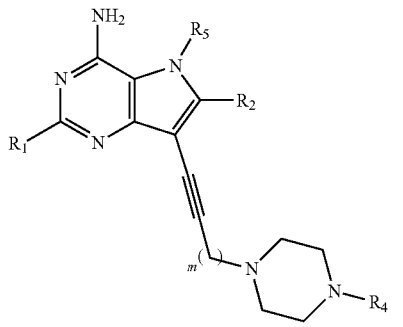

(III)

wherein $R_1$, $R_2$, $R_4$, $R_5$ and m are as hereinbefore defined with hydrogen in the presence of a catalyst.

For example a compound of formula (III) is dissolved in a suitable solvent, for example methyl alcohol or ethyl alcohol, and passed over a suitable catalyst, for example 10% palladium on carbon, in the presence of hydrogen at a suitable temperature, for example 20-60° C., in a suitable flow hydrogenation apparatus such as the Thales H-Cube™. The product (II) is isolated by removal of the solvent and purification if required.

When the $R_5$ protecting group is the BOM group the reaction to reduction the alkyne can result in the simultaneous removal of the protecting group to afford compounds of formula (I) directly.

A compound of formula (III) may be prepared by reaction of a compound of formula (IV):

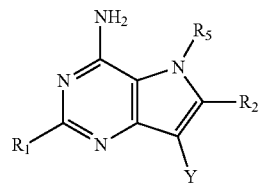

(IV)

wherein $R_1$, $R_2$ and $R_5$ are as hereinbefore defined and Y is a leaving group, for example a halogen such as iodine or bromine, or an alkyl sulfonate, such as a trifluoromethane sulfonate, with a compound of formula (V):

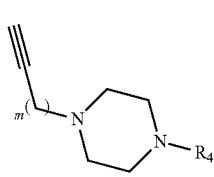

(V)

wherein $R_4$ and m are as defined hereinbefore.

For example a compound of formula (IV) and a compound of formula (V) are dissolved in a suitable solvent, for example DMF, in the presence of copper (I) iodide, a suitable catalyst, for example bis(triphenylphosphine)palladium(II) dichloride and a suitable base, for example triethylamine, and heated at a suitable temperature, for example 20-55° C. for a suitable period of time, for example 0.5-17 hours. The product (III) is isolated after an aqueous work-up and purification.

A compound of formula (V) may be prepared by reaction of a compound of formula (VI):

(VI)

wherein m is defined for a compound of formula (I) and X is a leaving group such as a halogen, for example chlorine, bromine or iodine, or an alkyl sulfonate, for example p-toluenesulfonate, with a compound of formula (VII):

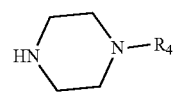

(VII)

wherein $R_4$ is as defined hereinbefore.

For example a compound of formula (VI), a compound of formula (VII) and a suitable base, for example sodium hydrogen carbonate, are dissolved in a suitable solvent, for example N,N-dimethylformamide, and heated at a suitable temperature, for example 80-100° C. for a suitable period of time, for example 16-18 hours. The product (V) is isolated after aqueous work-up and purification.

Compounds of formula (VI) and formula (VII) are either commercially available or may be prepared by methods described in the literature.

Alternatively, a compound of formula (III) may be prepared by reaction of a compound of formula (VIII):

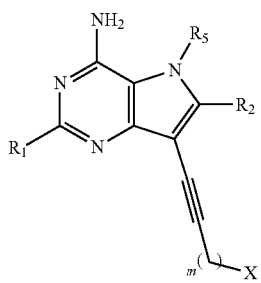

(VIII)

wherein $R_1$, $R_2$, $R_5$ and m are as hereinbefore defined and X is a leaving group as defined for compounds of formula (VI) with a compound of formula (VII):

For example a compound of formula (VIII), a compound of formula (VII) and a suitable base, for example triethylamine, are dissolved in a suitable solvent, for example acetontrile and heated at a suitable temperature, for example 60-80° C. for a suitable period of time, for example 16-26 hours. The product (III) is isolated after an aqueous work-up and purification.

Compounds of formula (VIII) can be prepared by reaction of compounds of formula (IV) with compounds of formula (VI). For example a compound of formula (IV), a compound of formula (VI) are dissolved in a suitable solvent, for example DMF, in the presence of copper(I) iodide, a suitable catalyst, for example bis(triphenylphosphine)palladium(II) dichloride and a suitable base, for example triethylamine, and heated at a suitable temperature, for example 20° C. for a suitable period of time, for example 18-20 hours. The product (VIII) is isolated after an aqueous work-up and purification.

Alternatively, a compound of formula (II) may also be prepared by the reaction of a compound of formula (II) wherein $R_4$=H. For example a suitable reducing agent, for example sodium triacetoxyborohydride is added to a mixture of a compound of formula (II) wherein $R_4$=H, a compound of formula (VII) and a drying agent, for example 4 Å molecular sieves, in a suitable solvent, for example dichloromethane, and stirred at a suitable temperature, for example 20° C., for a suitable period of time, for example 2-16 hours. The compound of formula (II) is isolated after an aqueous work-up and purification.

Furthermore, a compound of formula (II) may also be prepared by reaction of compounds of formula (IX)

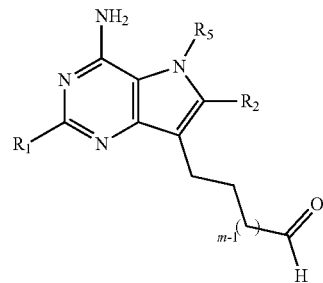

(IX)

wherein $R_1$, $R_2$, $R_5$ and m are as hereinbefore defined.

For example a suitable reducing agent, for example sodium triacetoxyborohydride is added to a mixture of a compound of formula (IX), a compound of formula (VII) and a drying agent, for example 4 Å molecular sieves, in a suitable solvent, for example dichloromethane, and stirred at a suitable temperature, for example 20° C., for a suitable period of time, for example 2-16 hours. The compound of formula (II) is isolated after an aqueous work-up and purification Compounds of formula (IX) may be prepared by reaction of compounds of formula (X):

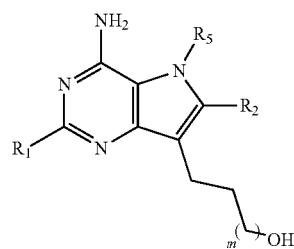

(X)

wherein $R_1$, $R_2$, $R_5$ and m are as hereinbefore defined.

For example a compound of formula (X), a suitable oxidant, for example tetrapropylammonium perruthenate in the presence of 4-methylmorpholine N-oxide, in a suitable solvent, for example a mixture of dichloromethane and acetonitrile, was stirred at a suitable temperature, for example 20° C., for a suitable period of time, for example 2 hours. The compound of formula (IX) isolated by removal of the solvent and purification if required.

Compounds of formula (X) may be prepared by reaction of compounds of formula (XI):

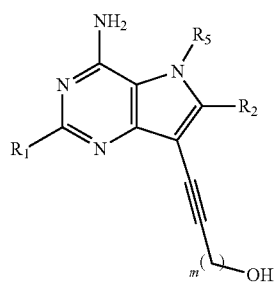

(XI)

wherein $R_1$, $R_2$, $R_5$ and m are as hereinbefore defined.

Compounds of formula (X) may be prepared by reaction of compounds of formula (XI) with hydrogen in the presence of a catalyst. For example a compound of formula (XI) is dissolved in a suitable solvent, for example ethanol, and passed over a suitable catalyst, for example 10% palladium on carbon in the presence of hydrogen, at a suitable temperature, for example 20-60° C. in an apparatus such as the Thales H-cube™. The compound of formula (X) is isolated by removal of the solvent and purification if required.

Compounds of formula (XI) can be prepared by reaction of compounds of formula (IV) with appropriate alkyn-1-ols. For example a compound of formula (IV) and a an alkyn-1-ol are dissolved in a suitable solvent, for example DMF, in the presence of copper (I) iodide, a suitable catalyst, for example bis(triphenylphosphine)palladium(II) dichloride and a suitable base, for example triethylamine, and heated at a suitable temperature, for example 20° C. for a suitable period of time, for example 1-17 hours. The compound of formula (XI) is isolated after an aqueous work-up and purification.

Compounds of formula (IV) may be prepared by reaction of compounds of formula (XII):

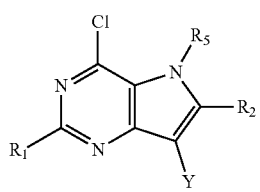

(XII)

wherein $R_1$, $R_2$ and $R_5$ are as hereinbefore defined and Y is defined for a compound of formula (IV) with a solution of ammonia.

For example, a solution of aqueous ammonia (0.88) is added to a solution of a compound of formula (XII) in a suitable solvent, for example iso-propyl alcohol. The resultant mixture is then heated in a microwave heater at a suitable temperature, for example 120-150° C. for a suitable period of time, for example 1-2 hours. The product (IV) is isolated after an aqueous work-up and purification.

Compounds of formula (XII) may be prepared by reaction of compounds of formula (XIII):

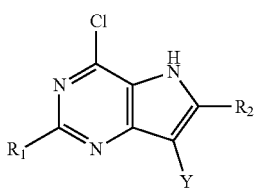

(XIII)

wherein $R_1$ and $R_2$ are as hereinbefore defined for a compound of formula (I) with a compound of formula (XIV):

(XIV)

wherein compound of formula (XIV) is a suitable precursor to the protecting group $R_5$, for example benzyl chloromethyl ether or (2-(chloromethoxy)ethyl)trimethylsilane.

For example a compound of formula (XIII) in a suitable solvent, for example N,N-dimethylformamide or tetrahydrofuran, is treated with a suitable base, for example a suspension of sodium hydride in oil. A compound of formula (XIV), for example benzyl chloromethyl ether or (2-(chloromethoxy)ethyl)trimethylsilane is added the reaction mixture is stirred at a suitable temperature, for example 20° C. for a suitable period of time, for example 1-4 hours. The compound of formula (XII) is isolated after an aqueous work-up and purification.

Compounds of formula (XIII) may be prepared by reaction of compounds of formula (XV):

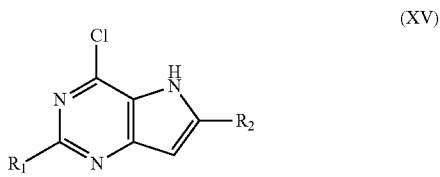

(XV)

wherein $R_1$ and $R_2$ are as hereinbefore defined for a compound of formula (I) with a halogenating reagent, for example N-iodosuccinimide.

A compound of formula (XV) is dissolved in a suitable solvent, for example tetrahydrofuran, is reacted with N-iodosuccinimide at suitable temperature, for example 20° C. for a suitable period of time, for example 1-2 hours. The compound of formula (XIII) is isolated after an aqueous work-up and purification.

Compounds of formula (XV) may be prepared by reaction of compounds of formula (XVI):

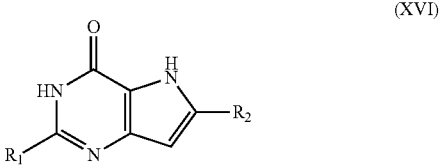

(XVI)

wherein $R_1$ and $R_2$ are as hereinbefore defined for a compound of formula (I) with a chlorinating reagent, for example phosphorus oxychloride.

A compound of formula (XVI) is suspended in phosphorus oxychloride and heated at a suitable temperature, for example 120° C. for a suitable period of time, for example 3-4 hours. Excess phosphorus oxychloride may be removed in vacuo then the residue is poured onto ice and the pH of the mixture adjusted to 7-9. The product is then extracted into a suitable organic solvent, for example ethyl acetate. The compound of formula (XV) is isolated by removal of the solvent and purification if required.

Compounds of formula (XVI) may be prepared by reaction of compounds of formula (XVII):

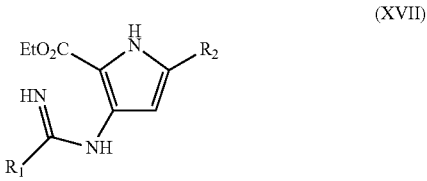

(XVII)

wherein $R_1$ and $R_2$ are as hereinbefore defined for a compound of formula (I) with a suitable base, for example sodium hydroxide.

A solution of compounds of formula (XVII) in a suitable solvent, for example ethyl alcohol, is treated with an aqueous solution of sodium hydroxide and the reaction mixture stirred at a suitable temperature, for example 80-100° C. for a suitable period of time, for example 4-18 hours. The compound of formula (XVI) is isolated after an aqueous work-up and purification.

Compounds of formula (XVII) can be prepared by reaction of compounds of formula (XVIII):

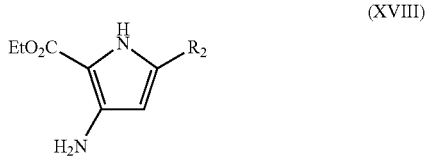

(XVIII)

with compounds of formula (XIX):

(XIX)

wherein $R_1$ and $R_2$ are as defined hereinbefore for a compound of formula (I).

For example a suspension of a compound of formula (XVIII) in a compound of formula (XIX) is treated with a solution of hydrogen chloride in a suitable solvent, for example a solution of hydrogen chloride in 1,4-dioxane is heated at a suitable temperature, 50-70° C. for a suitable period of time, for example 16-18 hours. The compound of formula (XVII) is isolated after filtration after the addition of a suitable solvent, for example tert-butyl methyl ether.

Alternatively, a compound of formula (XVI) can be prepared by reaction of compounds of formula (XVIII) with compounds of formula (XX):

(XX)

wherein $R_1$ is as defined hereinbefore for a compound of formula (I).

For example a mixture of compounds of formula (XVIII) and compounds of formula (XX) are heated in a suitable solvent, for example o-xylene, at a suitable temperature, for example reflux, for a suitable period of time, for example, 3 days. After cooling to ambient temperature the product (XVI) is isolated after filtration.

Compounds of formulae (VI), (VII), (XIV), (XVIII), (XIX) and (XX) are either known in the literature or are commercially available, for example from Sigma Aldrich, UK, or may be prepared by analogy with known procedures, for example those disclosed in standard reference texts of synthetic methodology such as J. March, Advanced Organic Chemistry, 6th Edition (2007), *WileyBlackwell, or Comprehensive Organic Synthesis* (Trost B. M. and Fleming I., (Eds.), Pergamon Press, 1991), each incorporated herein by reference as it relates to such procedures.

Examples of other protecting groups that may be employed in the synthetic routes described herein and the means for their removal can be found in T. W. Greene '*Protective Groups in Organic Synthesis*'; 4th Edition, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulphate, or anhydrous sodium sulphate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times temperatures may typically be determined by reaction-monitoring techniques, for example thin-layer chromatography and LC-MS.

Where appropriate individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

Methods of Use

Examples of disease states in which the compounds of formula (I) and pharmaceutically acceptable salts thereof have potentially beneficial effects include allergic diseases and other inflammatory conditions for example allergic rhinitis and asthma, infectious diseases, and cancer. The compounds of formula (I) and pharmaceutically acceptable salts thereof are also of potential use as vaccine adjuvants.

As modulators of the immune response the compounds of formula (I) and pharmaceutically acceptable salts thereof may also be useful in the treatment and/or prevention of immune-mediated disorders, including but not limited to inflammatory or allergic diseases such as asthma, allergic rhinitis and rhinoconjuctivitis, food allergy, hypersensitivity lung diseases, eosinophilic pneumonitis, delayed-type hypersensitivity disorders, atherosclerosis, pancreatitis, gastritis, colitis, osteoarthritis, psoriasis, sarcoidosis, pulmonary fibrosis, respiratory distress syndrome, bronchiolitis, chronic obstructive pulmonary disease, sinusitis, cystic fibrosis, actinic keratosis, skin dysplasia, chronic urticaria, eczema and all types of dermatitis.

The compounds of formula (I) and pharmaceutically acceptable salts thereof may also be useful in the treatment and/or prevention of reactions against respiratory infections, including but not limited to airways viral exacerbations and tonsillitis. The compounds may also be useful in the treatment and/or prevention of autoimmune diseases including but not limited to rheumatoid arthritis, psoriatic arthritis, systemic lupus erythematosus, Sjöegrens disease, ankylosing spondylitis, scleroderma, dermatomyositis, diabetes, graft rejection, including graft-versus-host disease, inflammatory bowel diseases including, but not limited to, Crohn's disease and ulcerative colitis.

The compounds of formula (I) and pharmaceutically acceptable salts thereof may also be useful in the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compounds of formula (I) and pharmaceutically acceptable salts thereof may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis.

The compounds of formula (I) and pharmaceutically acceptable salts thereof may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

It will be appreciated by those skilled in the art that references herein to treatment or therapy may, depending on the condition, extend to prophylaxis as well as the treatment of established conditions.

There is thus provided as a further aspect of the invention a compound of formula (I), or a pharmaceutically acceptable salt thereof, for use in therapy.

It will be appreciated that, when a compound of formula (I) or a pharmaceutically acceptable salt thereof is used in therapy, it is used as an active therapeutic agent.

There is also therefore provided a compound of formula (I), or a pharmaceutically acceptable salt thereof, for use in the treatment of allergic diseases and other inflammatory conditions, infectious diseases, and cancer.

There is also therefore provided a compound of formula (I), or a pharmaceutically acceptable salt thereof, for use in the treatment of allergic rhinitis.

There is also therefore provided a compound of formula (I), or a pharmaceutically acceptable salt thereof, for use in the treatment of asthma.

There is further provided the use of a compound of formula (I), or a pharmaceutically acceptable salt thereof, in the manufacture of a medicament for the treatment of allergic diseases and other inflammatory conditions, infectious diseases, and cancer.

There is further provided the use of a compound of formula (I), or a pharmaceutically acceptable salt thereof, in the manufacture of a medicament for the treatment of allergic rhinitis.

There is further provided the use of a compound of formula (I), or a pharmaceutically acceptable salt thereof, in the manufacture of a medicament for the treatment of asthma.

There is further provided a method of treatment of allergic diseases and other inflammatory conditions, infectious diseases, and cancer, which method comprises administering to a human subject in need thereof, a therapeutically effective amount of a compound of formula (I), or a pharmaceutically acceptable salt thereof.

There is further provided a method of treatment of allergic rhinitis, which method comprises administering to a human subject in need thereof, a therapeutically effective amount of a compound of formula (I), or a pharmaceutically acceptable salt thereof.

There is further provided a method of treatment of asthma, which method comprises administering to a human subject in need thereof, a therapeutically effective amount of a compound of formula (I), or a pharmaceutically acceptable salt thereof.

The compounds of formula (I) and pharmaceutically acceptable salts thereof are also of potential use as vaccine adjuvants.

There is thus provided as a further aspect of the invention a vaccine composition comprising a compound of formula (I), or a pharmaceutically acceptable salt thereof, and an antigen or antigen composition for use in therapy.

There is thus provided as a further aspect of the invention the use of a compound of formula (I), or a pharmaceutically acceptable salt thereof, and an antigen or antigen composition in the manufacture of a medicament for use in therapy.

There is further provided a method of treating or preventing disease comprising the administration to a human subject suffering from or susceptible to disease, a vaccine composition comprising a compound of formula (I), or a pharmaceutically acceptable salt thereof, and an antigen or antigen composition.

Compositions

The compounds of formula (I) and pharmaceutically acceptable salts thereof will normally, but not necessarily, be formulated into pharmaceutical compositions prior to administration to a patient. Accordingly, in another aspect of the invention there is provided a pharmaceutical composition comprising a compound of formula (I), or a pharmaceutically acceptable salt thereof, and one or more pharmaceutically acceptable excipients.

The compounds of formula (I) and pharmaceutically acceptable salts thereof may be formulated for administration in any convenient way. The compounds of formula (I) and pharmaceutically acceptable salts thereof may, for example, be formulated for oral, topical, inhaled, intranasal, buccal, parenteral (for example intravenous, subcutaneous, intradermal, or intramuscular) or rectal administration. In one aspect, the compounds of formula (I) and pharmaceutically acceptable salts thereof are formulated for oral administration. In a further aspect, the compounds of formula (I) and pharmaceutically acceptable salts thereof are formulated for topical administration, for example intranasal or inhaled administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of formula (I) or (a) pharmaceutically acceptable salt(s) thereof to be delivered to all areas of the nasal cavities (the target tissue) and further, may permit the compound(s) of formula (I) or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicel® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation.

Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. The compound of formula (I), or a pharmaceutically acceptable salt thereof, may be formulated as a suspension or solution. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. Alternatively, the fluid dispenser for delivery of a fluid composition to the nasal cavities may be designed to be dose-limited, for example a single use dispenser comprising a single dose. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). The dispenser has a housing which houses a fluid-discharge device having a compression pump mounted on a container for containing a fluid composition. The housing has at least one finger-operable side lever which is movable inwardly with respect to the housing to move the container upwardly in the housing by means of a cam to cause the pump to compress and pump a metered dose of the composition out of a pump stem through a nasal nozzle of the housing. In one embodiment, the fluid dispenser is of the general type illustrated in FIGS. 30-40 of WO 2005/044354.

Aqueous compositions containing a compound of formula (I) or a pharmaceutically acceptable salt thereof may also be delivered by a pump as disclosed in International Patent Application publication number WO2007/138084 (Glaxo Group Limited), for example as disclosed with reference to FIGS. 22-46 thereof, or as disclosed in United Kingdom patent application number GB0723418.0 (Glaxo Group Limited), for example as disclosed with reference to FIGS. 7-32 thereof. The pump may be actuated by an actuator as disclosed in FIGS. 1-6 of GB0723418.0.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (AstraZeneca), TWISTHALER™ (Schering) and CLICKHALER™ (Innovata.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDIHALER™ (Boehringer Ingelheim.)

Pressurised aerosol compositions suitable for inhalation can be either a suspension or a solution and may contain a compound of formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligo-lactic acid or derivative thereof e.g. as described in WO 94/21229 and WO 98/34596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, wool-fat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

The compounds of formula (I) and pharmaceutically acceptable salts thereof may, for example, be formulated for transdermal delivery by composition into patches or other devices (e.g. pressurised gas devices) which deliver the active component into the skin.

For buccal administration the compositions may take the form of tablets or lozenges formulated in the conventional manner.

The compounds of formula (I) and pharmaceutically acceptable salts thereof may also be formulated as suppositories, e.g. containing conventional suppository bases such as cocoa butter or other glycerides.

The compounds of formula (I) and pharmaceutically acceptable salts thereof may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds of formula (I) and pharmaceutically acceptable salts thereof may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of formula (I), or a pharmaceutically acceptable salt thereof.

There is further provided a vaccine composition comprising a compound of formula (I), or a pharmaceutically acceptable salt thereof, and an antigen or antigen composition.

The compounds of formula (I) and pharmaceutically acceptable salts thereof may be employed alone or in combination with other therapeutically-active agents. The invention provides in a further aspect, a combination comprising a compound of formula (I), or a pharmaceutically acceptable salt thereof, together with at least one other therapeutically-active agent.

The compounds of formula (I) and pharmaceutically acceptable salts thereof and the other therapeutically-active agent(s) may be administered together or separately and, when administered separately, administration may occur simultaneously or sequentially, in any order. The amounts of the compound(s) of formula (I) or (a) pharmaceutically acceptable salt(s) thereof and the other therapeutically-active agent(s) and the relative timings of administration will be selected in order to achieve the desired combined therapeutic effect. The administration of a combination of a compound of formula (I) or a pharmaceutically acceptable salt thereof with other treatment agents may be by administration concomitantly in a unitary pharmaceutical composition including both compounds, or in separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of formula (I) and pharmaceutically acceptable salts thereof may be used in combination with one or more agents useful in the prevention or treatment of viral infections. Examples of such agents include, without limitation; polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, and similar agents; entry inhibitors such as enfuvirtide (T-20), T-1249, PRO-542, PRO-140, TNX-355, BMS-806, 5-Helix and similar agents; integrase inhibitors such as L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents. The compounds of formula (I) and pharmaceutically acceptable salts thereof may also be used in combination with one or more other agents which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, antifibrotic agents, anti-inflammatory agents such as corticosteroids or NSAIDs (non-steroidal anti-inflammatory agents) and similar agents.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. entanercept and similar agents; antigen non-specific immunotherapies (e.g. interferon or other cytokines/chemokines, cytokine/chemokine receptor modulators, cytokine agonists or antagonists, TLR agonists and similar agents).

The compounds of formula (I) and pharmaceutically acceptable salts thereof may be used in combination with one or more other agents which may be useful in the prevention or treatment of cancer, for example chemotherapeutics such as alkylating agents, topoisomerase inhibitors, antimetabolites, antimitotic agents, kinase inhibitors and similar agents; monoclonal antibody therapy such as trastuzumab, gemtuzumab and other similar agents; and hormone therapy such as tamoxifen, goserelin and similar agents.

The pharmaceutical compositions according to the invention may also be used alone or in combination with at least one other therapeutic agent in other therapeutic areas, for example gastrointestinal disease. The compositions according to the invention may also be used in combination with gene replacement therapy.

The invention includes in a further aspect a combination comprising a compound of formula (I), or a pharmaceutically acceptable salt thereof, together with at least one other therapeutically active agent.

The combinations referred to above may conveniently be presented for use in the form of a pharmaceutical composition and thus pharmaceutical compositions comprising a combination as defined above together with at least one pharmaceutically acceptable diluent or carrier thereof represent a further aspect of the invention.

A therapeutically effective amount of a compound of formula (I) or a pharmaceutically acceptable salt thereof will depend upon a number of factors. For example, the species, age, and weight of the recipient, the precise condition requiring treatment and its severity, the nature of the composition, and the route of administration are all factors to be considered. The therapeutically effective amount ultimately should be at the discretion of the attendant physician. Regardless, an effective amount of a compound of the present invention for the treatment of humans suffering from frailty, generally, should be in the range of 0.0001 to 100 mg/kg body weight of recipient per day. More usually the effective amount should be in the range of 0.001 to 10 mg/kg body weight per day. Thus, for a 70 kg adult one example of an actual amount per day would usually be from 7 to 700 mg. For intranasal and inhaled routes of administration, typical doses for a 70 kg adult should be in the range of 0.1 micrograms to 1 mg per day, for example 1 µg, 10 µg or 100 µg. This amount may be given in a single dose per day or in a number (such as two, three, four, five, or more) of sub-doses per day such that the total daily dose is the same. An effective amount of a pharmaceutically acceptable salt of a compound of formula (I) may be determined as a proportion of the effective amount of the compound of formula (I) or a pharmaceutically acceptable salt thereof per se. Similar dosages should be appropriate for treatment of the other conditions referred to herein.

Compounds of formula (I) and pharmaceutically acceptable salts thereof may also be administered at any appropriate frequency e.g. 1-7 times per week. The precise dosing regimen will of course depend on factors such as the therapeutic indication, the age and condition of the patient, and the particular route of administration chosen. In one aspect of the invention, a compound of formula (I), or a pharmaceutically acceptable salt thereof, may be administered once weekly for a period of 4 to 8 weeks, for example 4, 5, 6, 7 or 8 weeks.

Pharmaceutical compositions may be presented in unit-dose forms containing a predetermined amount of active ingredient per unit dose. Such a unit may contain, as a non-limiting example, 0.5 mg to 1 g of a compound of formula (I) or a pharmaceutically acceptable salt thereof, depending on the condition being treated, the route of administration, and the age, weight, and condition of the patient. Preferred unit-dosage compositions are those containing a daily dose or sub-dose, as herein above recited, or an appropriate fraction thereof, of an active ingredient. Such pharmaceutical compositions may be prepared by any of the methods well-known in the pharmacy art.

There is also provided a process for preparing such a pharmaceutical composition which comprises admixing a compound of formula (I), or a pharmaceutically acceptable salt thereof, with one or more pharmaceutically acceptable excipients.

Abbreviations

The following list provides definitions of certain abbreviations as used herein. It will be appreciated that the list is not exhaustive, but the meaning of those abbreviations not herein below defined will be readily apparent to those skilled in the art.
DCM Dichloromethane
DMF N,N-Dimethylformamide
DMSO Dimethylsulphoxide
DME 1, 2-Dimethoxyethane
THF Tetrahydrofuran
EtOAc Ethyl acetate
MeOH Methanol
EtOH Ethanol
MeCN Acetonitrile
HCl Hydrochloric acid
HPLC High performance liquid chromatography
MDAP Mass Directed Autopreparative HPLC
SPE Solid phase extraction
MeOH Methanol
TFA Trifluoroacetic acid
DIPEA N,N-Diisopropylethylamine
TBME tert-Butyl methyl ether Experimental Details $^1$H NMR $^1$H NMR spectra were recorded in either CDCl$_3$ or DMSO-d$_6$ on either a Bruker DPX 400 or Bruker Avance DRX, Varian Unity 400 spectrometer or JEOL Delta all working at 400 MHz. The internal standard used was either tetramethylsilane or the residual protonated solvent at 7.25 ppm for CDCl$_3$ or 2.50 ppm for DMSO-d$_6$.

LCMS

System A
Column: 50 mm×2.1 mm ID, 1.7 μm Acquity UPLC BEH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 0.1% v/v formic acid in water
B: 0.1% v/v formic acid acetonitrile
Gradient:

| Time (min.) | A % | B % |
|---|---|---|
| 0 | 97 | 3 |
| 1.5 | 0 | 100 |
| 1.9 | 0 | 100 |
| 2.0 | 97 | 3 |

System B
Column: 50 mm×2.1 mm ID, 1.7 μm Acquity UPLC BEH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation
Solvents: A: 10 mM ammonium bicarbonate in water adjusted to pH10 with ammonia solution
B: acetonitrile
Gradient:

| Time (min.) | A % | B % |
|---|---|---|
| 0 | 99 | 1 |
| 1.5 | 3 | 97 |
| 1.9 | 3 | 97 |
| 2.0 | 0 | 100 |

Mass Directed Autopreparative HPLC (MDAP)

Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method A
Method A was conducted on a Sunfire C$_{18}$ column (typically 150 mm×30 mm i.d. 5 μm packing diameter) at ambient temperature. The solvents employed were:
A=0.1% v/v solution of formic acid in water
B=0.1% v/v solution of formic acid in acetonitrile.

Method B
Method B was conducted on an XBridge C$_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.

Method C Method C was conducted on a Sunfire C$_{18}$ column (typically 150 mm×30 mm i.d. 5 μm packing diameter) at ambient temperature. The solvents employed were:
A=0.1% v/v solution of trifluoroacetic acid in water
B=0.1% v/v solution of trifluoroacetic acid in acetonitrile.

Intermediate Preparation

Intermediate 1: Ethyl 3-pentanimidamido-1H-1-pyrrole-2-carboxylate hydrochloride A solution of hydrogen chloride in dioxane (12 mL, 4M, 48 mmol) was added dropwise to a suspension of ethyl 3-amino-1H-pyrrole-2-carboxylate hydrochloride (2.04 g, 10.7 mmol) (J. Org. Chem. 1999, 64(22), 8411) in valeronitrile (30 mL). The resultant mixture was heated at 50° C. for 18 hours. The reaction mixture was cooled to room temperature and the solid material collected by filtration and washed with TBME. The title compound was obtained as an off-white solid (2.19 g). A further portion of TBME was added to the filtrate and the mixture re-filtered, the precipitate was washed with TBME and dried to give an additional portion of the title compound (0.275 g).

$^1$H NMR (400 MHz, DMSO-d$_6$) δ ppm 12.22 (br. s., 1H) 10.88 (s, 1H) 9.39 (br. s., 1H) 8.25 (br. s., 1H) 7.09 (t, J=2.9 Hz, 1H) 6.19 (t, J=2.5 Hz, 1H) 4.23 (q, J=7.0 Hz, 2H) 2.52-2.60 (m, 2H) 1.63-1.77 (m, 2H) 1.34-1.47 (m, 2H) 1.27 (t, J=7.2 Hz, 3H) 0.94 (t, J=7.4 Hz, 3H)

Intermediate 2: 2-Butyl-3H-pyrrolo[3,2-d]pyrimidin-4(5H)-one

A solution of sodium hydroxide (1.44 g, 35.9 mmol) in water (7 mL) was added to a solution of ethyl 3-pentanimidamido-1H-pyrrole-2-carboxylate hydrochloride (2.46 g, 8.99 mmol) in ethanol (30 mL). The resultant mixture was heated at reflux for a total of 4 hours. The reaction mixture was cooled to room temperature and the pH adjusted to pH 6.5 with aqueous citric acid. The resultant mixture was extracted with ethyl acetate (2×50 mL). The combined organic phases were washed with saturated aqueous sodium chloride solution, dried (Na$_2$SO$_4$), filtered and evaporated to give the title compound as a pale brown solid (1.69 g).

LCMS (System B): t$_{RET}$=0.66 min; MH$^+$ 192

Intermediate 3: 2-Butyl-4-chloro-5H-pyrrolo[3,2-d]pyrimidine

Phosphorus oxychloride (20 mL, 21.46 mmol) was added to 2-butyl-3H-pyrrolo[3,2-d]pyrimidin-4(5H)-one (1.69 g). The resultant mixture was heated at 100° C. After 4 hours the reaction mixture was cooled to room temperature then poured onto ice. The aqueous phase was treated with aqueous sodium hydroxide solution (5M) until the pH was 7. The resultant mixture was extracted with ethyl acetate (2×150 mL). The combined organic phase were washed with brine, dried (Na$_2$SO$_4$), filtered and evaporated to give the title compound (1.69 g)

LCMS (System B): t$_{RET}$=0.90 min; MH$^+$ 210, 212

Intermediate 4: 2-Butyl-4-chloro-7-iodo-5H-pyrrolo[3,2-d]pyrimidine

N-Iodosuccinimide (2.09 g, 9.29 mmol) was added portionwise to a stirred solution of 2-butyl-4-chloro-5H-pyrrolo[3,2-d]pyrimidine (1.69 g, 8.06 mmol) in THF (35 mL). The resultant mixture was stirred at room temperature for 1 hour. The reaction mixture was diluted with TBME (50 mL) then washed with aqueous sodium thiosulphate solution (50 mL)

then saturated aqueous sodium chloride solution (20 mL). The organic phase was dried (Na$_2$SO$_4$), filtered and evaporated. The sample was dissolved in dichloromethane and purified by chromatography on silica using a gradient of 0-100% dichloromethane-cyclohexane over 30 minutes followed by a gradient of 0-100% TBME-cyclohexane followed by 0-20% methanol over 15 minutes. The appropriate fractions were identified by LC-MS then combined and evaporated in vacuo to give the title compound as a yellow solid (2.2 g).

LCMS (System B): $t_{RET}$=1.14 min; MH$^+$ 336, 338

Intermediate 5: 5-((Benzyloxy)methyl)-2-butyl-4-chloro-7-iodo-5H-pyrrolo[3,2-d]pyrimidine Sodium hydride (0.338 g, 60% in oil, 14.08 mmol) was added portionwise to a stirred solution of 4-chloro-7-iodo-2-butyl-5H-pyrrolo[3,2-d]pyrimidine (2.19 g, 6.53 mmol) in DMF (30 mL) cooled in an ice-bath. After 30 minutes benzyl chloromethyl ether (1.13 mL, 1.278 g, 8.16 mmol) was added and the reaction stirred at room temperature. The reaction mixture was quenched with water and the resultant mixture partitioned between ethyl acetate (150 mL) and water (150 mL). The organic phase was washed with water then saturated aqueous sodium chloride solution, dried (Na$_2$SO$_4$), filtered and evaporated. The sample was dissolved in dichloromethane and purified by chromatography on silica (100 g) using a gradient of 0-100% ethyl acetate-cyclohexane over 30 minutes. The appropriate fractions were combined and evaporated in vacuo to give the title compound as a yellow oil (2.82 g).

LCMS (System B): $t_{RET}$=1.49 min; MH$^+$ 456, 458

Intermediate 6: 5-((Benzyloxy)methyl)-2-butyl-7-iodo-5H-pyrrolo[3,2-d]pyrimidin-4-amine 5-((Benzyloxy)methyl)-2-butyl-4-chloro-7-iodo-5H-pyrrolo[3,2-d]pyrimidine (1 g, 2.2 mmol) was suspended in 2-propanol (5 mL) and 35% (0.88) ammonia solution (4 mL). The reaction was stirred at 120° C. for 90 minutes in a Biotage Initiator microwave. A further 1 mL of 35% (0.88) ammonia solution was added to the reaction. The reaction was stirred at 120° C. for 90 minutes in a Biotage Initiator microwave. The reaction was evaporated in vacuo to yield a pale yellow oil. The oil was dissolved in the minimum volume of 20% methanol in dichloromethane and purified by chromatography on silica using a gradient of 0-100% ethyl acetate in cyclohexane gradient over 80 minutes. Fractions were combined and evaporated in vacuo to yield the title compound as a colourless oil (768 mg).

LCMS (System B): $t_{RET}$=1.19 min; MH$^+$ 437

Intermediate 7: Ethyl 5-methyl-3-pentanimidamido-1H-pyrrole-2-carboxylate hydrochloride Hydrogen chloride in dioxane (4M, 308 mL, 1.2 mol) was added dropwise to ethyl 3-amino-5-methyl-1H-pyrrole-2-carboxylate (38.3 g, 228 mmol) (J. Med. Chem. 2008, 51, 68) in valeronitrile (383 mL). The resultant mixture was heated at 50° C. overnight. An additional portion of acid (160 mL, 0.64 mol) was added and the mixture heated at 55° C. overnight. The reaction mixture was cooled to room temperature, filtered and the filtrate evaporated. The residue was slurried in TBME (1200 mL) for 30 minutes then the solid filtered and washed with TMBE and dried. The title compound was obtained as a brown solid (58.9 g).

$^1$H NMR (400 MHz, DMSO-d$_6$) δ ppm includes 11.90 (br. s, 1H) 11.09 (s, 1H) 9.52 (br. s, 1H) 8.14 (br. s, 1H) 5.82 (br. s, 1H) 4.12 (q, J=7.1 Hz, 2H) 3.48 (br. s, 1H) 2.14 (s, 3H) 1.51-1.70 (m, 2H) 1.05-1.40 (m, 6H) 0.84 (t, J=7.1 Hz, 3H)

Intermediate 8: 2-Butyl-6-methyl-3H-pyrrolo[3,2-d]pyrimidin-4(5H)-one

Aqueous sodium hydroxide solution (6M, 138 mL) was added dropwise to a solution of ethyl 5-methyl-3-pentanimidamido-1H-pyrrole-2-carboxylate (58.9 g, 0.2 mol) in ethanol (550 mL) cooled in an ice-bath. The reaction mixture was heated at reflux for 2.5 hours then cooled to room temperature. Water (700 mL) was added and the pH adjusted to pH 6.5 using aqueous citric acid (2M). The resultant mixture was stirred for 45 minutes then filtered and the solid material washed with water. The material was dried in a vacuum oven at 50° C. to give the title compound.

$^1$H NMR (400 MHz, DMSO-d$_6$) δ ppm includes 11.60 (s, 1H) 11.53 (s, 1H) 5.91 (s, 1H) 2.33-2.50 (m, 2H) 2.19 (s, 3H) 1.45-1.60 (m, 2H) 1.10-1.26 (m, 2H) 0.70-0.84 (m, 3H)

Intermediate 9: 2-Butyl-4-chloro-6-methyl-5H-pyrrolo[3,2-d]pyrimidine

Phosphorus oxychloride (42.8 mL, 70.4 g, 0.459 mol) was added dropwise to a solution of 2-butyl-6-methyl-3H-pyrrolo[3,2-d]pyrimidin-4(5H)-one (37.5 g, 0.183 mol) in acetonitrile (750 mL) under an atmosphere of nitrogen. The reaction mixture was heated at reflux overnight. After cooling to room temperature an additional portion of phosphorus oxychloride (42.8 mL, 70.4 g, 0.459 mol) was added dropwise and heating continued for a further 3.5 hours. The reaction was cooled to room temperature again and a further portion of phosphorus oxychloride (42.8 mL, 70.4 g, 0.459 mol) was added dropwise and heating continued for 3 hours. The reaction mixture was allowed to stand at room temperature overnight then heated at reflux for 3.5 hours. The reaction mixture was cooled then concentrated. The residue was cooled in an ice-bath and ice-cold water (650 mL) was added carefully. The pH was adjusted to 8 using aqueous potassium hydroxide solution and then mixture stirred for 45 minutes. The mixture was partitioned between dichloromethane (1000 mL) and water (1000 mL). The aqueous layer and solid material was re-extracted with dichloromethane (2×500 mL). The combined organic layers were dried (Na$_2$SO$_4$) and filtered through a plug of neutral alumina. The filtrate was concentrated to a yellow oil, a seed crystal and hexane were added. The solid material was filtered, washed with hexane and dried to give the title compound as an off-white solid (15.5 g).

LCMS (System A): $t_{RET}$=0.81 min; MH$^+$ 224/226

Intermediate 10: 2-Butyl-4-chloro-7-iodo-6-methyl-5H-pyrrolo[3,2-d]pyrimidine

Prepared similarly to Intermediate 4 from. 2-butyl-4-chloro-6-methyl-5H-pyrrolo[3,2-d]pyrimidine.

LCMS (System B): $t_{RET}$=1.20 min; MH$^+$ 350, 352

Intermediate 11: 5-((Benzyloxy)methyl)-2-butyl-4-chloro-7-iodo-6-methyl-5H-pyrrolo[3,2-d]pyrimidine Prepared similarly to Intermediate 5 from 2-butyl-4-chloro-7-iodo-6-methyl-5H-pyrrolo[3,2-d]pyrimidine LCMS (System B): $t_{RET}$=1.54 min; MH$^+$ 470, 472

Intermediate 12: 5-((Benzyloxy)methyl)-2-butyl-7-iodo-6-methyl-5H-pyrrolo[3,2-d]pyrimidin-4-amine Prepared similarly to Intermediate 6 from 5-((benzyloxy)methyl)-2-butyl-4-chloro-7-iodo-6-methyl-5H-pyrrolo[3,2-d]pyrimidine LCMS (System B): $t_{RET}$=1.24 min; MH$^+$ 451

Intermediate 13: 5-((Benzyloxy)methyl)-2-butyl-7-(5-chloropent-1-yn-1-yl)-5H-pyrrolo[3,2-d]pyrimidin-4-amine To a degassed suspension of 5-((benzyloxy)methyl)-2-butyl-7-iodo-5H-pyrrolo[3,2-d]pyrimidin-4-amine (2.768 g, 6.34 mmol), copper (I) iodide (0.242 g, 1.269 mmol), and bis(triphenylphosphine)palladium(II)dichloride (0.445 g, 0.634 mmol) in anhydrous N,N-dimethylformamide (40 mL) was added a solution of 5-chloropent-1-yne (0.781 g, 7.61 mmol) and triethylamine (1.231 mL, 8.88 mmol) in anhydrous N,N-dimethylformamide (20 mL) dropwise over 2 minutes. The reaction was stirred at ambient temperature for 17 hours. The reaction was concentrated in vacuo and the resultant brown oil partitioned between water (500 mL) and ethyl acetate (500 mL). The organic was separated and the aqueous back extracted with ethyl acetate (250 mL). The combined organics were washed with brine (400 mL), dried (MgSO$_4$), filtered and concentrated in vacuo. The sample was dissolved in dichloromethane and purified by chromatography on silica (Si) (2×100 g) using a 0-100% ethyl acetate-cyclohexane gradient over 60 minutes. The appropriate fractions were combined and evaporated in vacuo to give a red oil. The sample was dissolved in dichloromethane and purified by chromatography on silica using a 0-100% ethyl acetate-cyclohexane gradient over 80 minutes. The appropriate fractions were combined and evaporated in vacuo to give the title compound as a yellow solid. (1.13 g).

LCMS (System B): $t_{RET}$=1.29 min; MH$^+$ 411, 413

Intermediate 14: tert-Butyl 4-(5-(4-amino-5-((benzyloxy)methyl)-2-butyl-5H-pyrrolo[3,2-d]pyrimidin-7-yl)pent-4-yn-1-yl)piperazine-1-carboxylate To a solution of 5-((benzyloxy)methyl)-2-butyl-7-(5-chloropent-1-yn-1-yl)-5H-pyrrolo[3,2-d]pyrimidin-4-amine (100 mg, 0.243 mmol) in anhydrous N,N-dimethylformamide (2 mL) was added 1-BOC-piperazine (50 mg, 0.268 mmol) and triethylamine (51 vL, 0.366 mmol). The reaction was stirred at 70° C. for 22 hours. A further 100 mg (0.537 mmol) of 1-BOC-piperazine and 0.1 mL (0.717 mmol) of triethylamine was added to the reaction. The reaction was stirred at 70° C. for a further 24 hours. The cooled reaction was evaporated in vacuo and partitioned between dichloromethane and water. The organic layer was passed through a hydrophobic frit and evaporated in vacuo to yield a yellow oil. The oil was dissolved in MeOH:DMSO (1:1) (2×1 mL) and purified by MDAP (Method B). Appropriate fractions were combined and evaporated in vacuo to yield the title compound as a colourless oil (80 mg).

LCMS (System B): $t_{RET}$=1.35 min; MH$^+$ 561.

Intermediate 15: 1-iso-Propyl-4-(pent-4-yn-1-yl)piperazine

A mixture of 1-(1-methylethyl)piperazine (6 g, 46.8 mmol), 5-chloro-1-pentyne (4.91 mL, 46.8 mmol) and sodium bicarbonate (3.93 g, 46.8 mmol) in N,N-dimethylformamide (75 mL) was heated at 80° C. overnight. The reaction mixture was cooled to room temperature then partitioned between ether (100 mL) and water (100 mL). The organic phase was washed with brine (25 mL) then dried using a hydrophobic frit and evaporated. The crude material was purified on a 50 g SCX cartridge (preconditioned with MeOH) eluted with MeOH and flushed with 2M NH$_3$/MeOH. The appropriate fractions were concentrated and dried under vacuum to obtain the title compound as a light brown oil (3.22 g).

$^1$H NMR (400 MHz, CDCl$_3$) contains the following signals δ ppm 2.39-2.69 (m, 10H) 2.19-2.27 (m, 2H) 1.93-1.97 (m, 1H) 1.67-1.78 (m, 2H) 1.01-1.10 (m, 6H)

Intermediate 16: 5-((Benzyloxy)methyl)-2-butyl-7-(5-(4-isopropylpiperazin-1-yl)pent-1-yn-1-yl)-5H-pyrrolo[3,2-d]pyrimidin-4-amine To a degassed solution of 5-((benzyloxy)methyl)-2-butyl-7-iodo-5H-pyrrolo[3,2-d]pyrimidin-4-amine (223 mg, 0.511 mmol) in anhydrous N,N-dimethylformamide (3.5 mL) under a nitrogen atmosphere at room temperature was added copper(I) iodide (19 mg, 0.10 mmol), bis(triphenylphosphine)palladium(II)dichloride (40 mg, 0.057 mmol) and finally triethylamine (0.128 mL, 0.920 mmol). The mixture was stirred at room temperature under a nitrogen atmosphere for 10 minutes and then a solution of 1-(1-methylethyl)-4-(4-pentyn-1-yl)piperazine (159 mg, 0.818 mmol) in anhydrous degassed N,N-dimethylformamide (0.5 mL) was added. The reaction mixture was stirred at 55° C. for 40 minutes. A solution of 1-(1-methylethyl)-4-(4-pentyn-1-yl)piperazine 60 mg (0.309 mmol) in anhydrous degassed N,N-dimethylformamide (0.5 mL) was added. The reaction mixture was stirred at 55° C. for 30 minutes. The reaction was evaporated in vacuo to yield a dark yellow oil. The oil was partitioned between water and dichloromethane. The organic layer was separated and the aqueous back extracted with dichloromethane. The combined organic extracts were passed through a hydrophobic frit and evaporated in-vacuo to yield a dark yellow oil. The oil was dissolved in MeOH:DMSO (1:1) (4×1 mL) and purified by MDAP (Method B) Appropriate fractions were combined and evaporated in vacuo to yield the title compound as a yellow oil (80 mg).

LCMS (System B): $t_{RET}$=1.17 min; MH$^+$ 503.

Intermediate 17: 5-((Benzyloxy)methyl)-2-butyl-7-(5-(4-isopropylpiperazin-1-yl)pent-1-yn-1-yl)-6-methyl-5H-pyrrolo[3,2-d]pyrimidin-4-amine To a degassed solution of 5-((benzyloxy)methyl)-2-butyl-7-iodo-6-methyl-5H-pyrrolo[3,2-d]pyrimidin-4-amine (159 mg, 0.353 mmol) in anhydrous N,N-dimethylformamide (3 mL) under a nitrogen atmosphere at room temperature was added copper (I) iodide (19 mg, 0.100 mmol), bis(triphenylphosphine)palladium(II)dichloride (40 mg, 0.057 mmol) and finally triethylamine (0.088 mL, 0.636 mmol). The mixture was stirred at room temperature under a nitrogen atmosphere for 10 minutes and then a solution of 1-(1-methylethyl)-4-(4-pentyn-1-yl)piperazine (110 mg, 0.565 mmol) in anhydrous degassed N,N-dimethylformamide (1 mL) was added. The reaction mixture was stirred at 55° C. for 40 minutes. Additional 1-(1-methylethyl)-4-(4-pentyn-1-yl)piperazine (110 mg, 0.565 mmol) was added and the reaction mixture was left to stir at 55° C. for 4 5 minutes. 1-(1-methylethyl)-4-(4-pentyn-1-yl)piperazine (110 mg, 0.565 mmol) was added and the reaction mixture was left to stir at 55° C. for 45 minutes. The reaction was evaporated in vacuo to yield a dark yellow oil. The oil was partitioned between water and dichloromethane. The organic layer was separated and the aqueous back extracted with dichloromethane. The combined organic extracts were passed through a hydrophobic frit and evaporated in vacuo to yield a dark yellow oil. The crude product was dissolved in 6 mL of 50:50 DMSO/MeOH and purified by MDAP (Method B). Fractions which contained product were concentrated to give the title compound as a yellow oil (61 mg).

LCMS (System B): $t_{RET}$=1.22 min; MH$^+$ 517.

Intermediate 18: 5-((Benzyloxy)methyl)-2-butyl-7-(5-(4-ethylpiperazin-1-yl)pent-1-yn-1-yl)-6-methyl-5H-pyrrolo[3,2-d]pyrimidin-4-amine Prepared similarly to Intermediate 17 from 5-((benzyloxy)methyl)-2-butyl-7-iodo-6-methyl-5H-pyrrolo[3,2-d]pyrimidin-4-amine and 1-ethyl-4-(pent-4-yn-1-yl)piperazine (Bioorg. Med. Chem. Lett. 2011, 21(6), 1601; WO2006/105372).

LCMS (System B): $t_{RET}$=1.17 min; MH$^+$ 503

Intermediate 19: tert-Butyl 4-(3-(4-amino-5-((benzyloxy)methyl)-2-butyl-5H-pyrrolo[3,2-d]pyrimidin-7-yl)prop-2-yn-1-yl)piperazine-1-carboxylate To a degassed solution of 5-((benzyloxy)methyl)-2-butyl-7-iodo-5H-pyrrolo[3,2-d]pyrimidin-4-amine (150 mg, 0.344 mmol) in anhydrous N,N-dimethylformamide (3 mL) under nitrogen atmosphere at room temperature was added copper (I) iodide (13 mg, 0.068 mmol), bis(triphenylphosphine)palladium(II)dichloride (27 mg, 0.038 mmol) and, finally, triethylamine (0.086 mL, 0.619 mmol). The mixture was stirred at room temperature under nitrogen atmosphere for 10 minutes and then tert-butyl 4-(prop-2-yn-1-yl)piperazine-1-carboxylate (139 mg, 0.619 mmol) was added in one portion. The reaction mixture was heated to 55° C. in a pre-heated oil bath and stirred at 55° C. for 40 minutes. The reaction was evaporated in vacuo to yield a dark brown oil. The oil was partitioned between water and dichloromethane. The organic layer was separated and the aqueous back extracted with dichloromethane. The combined organic extracts were passed through a hydrophobic frit and evaporated in vacuo to yield a dark brown oil. The oil was dissolved in MeOH:DMSO (1:1) (2×1 mL) and purified by MDAP (Method B). Appropriate fractions were combined and evaporated in vacuo to yield the title compound as a brown oil (180 mg).

LCMS (System B): $t_{RET}$=1.26 min; MH$^+$ 533

Intermediate 20: 5-((Benzyloxy)methyl)-2-butyl-7-(3-(piperazin-1-yl)prop-1-yn-1-yl)-5H-pyrrolo[3,2-d]pyrimidin-4-amine To a solution of tert-butyl 4-(3-(4-amino-5-((benzyloxy)methyl)-2-butyl-5H-pyrrolo[3,2-d]pyrimidin-7-yl)prop-2-yn-1-yl)piperazine-1-carboxylate (85 mg, 0.160 mmol) in anhydrous methanol (5 mL) was added 4M hydrogen chloride in 1,4-dioxane (0.5 ml, 2.0 mmol). The reaction was stirred at room temperature for 19 hours. A further 0.5 mL (2.0 mmol) of 4M hydrogen chloride in 1,4-dioxane was added to the reaction. Reaction stirred at room temperature for 2 hours. The reaction was evaporated to dryness under a stream of nitrogen to yield a green oil. The oil was dissolved in MeOH:DMSO (1:1) (2×1 mL) and purified by MDAP (Method B). Appropriate fractions were combined and evaporated in-vacuo to yield the title compound as a pale yellow oil (38 mg).

LCMS (System B): $t_{RET}$=0.97 min; MH$^+$ 433

Intermediate 21: 5-((Benzyloxy)methyl)-2-butyl-7-(3-(4-ethylpiperazin-1-yl)prop-1-yn-1-yl)-5H-pyrrolo[3,2-d]pyrimidin-4-amine To a solution of 5-((benzyloxy)methyl)-2-butyl-7-(3-(piperazin-1-yl)prop-1-yn-1-yl)-5H-pyrrolo[3,2-d]pyrimidin-4-amine (38 mg, 0.088 mmol) in anhydrous N,N-dimethylformamide (1 mL) at room temperature was added triethylamine (25 µL, 0.179 mmol) and iodoethane (10 µL, 0.125 mmol). The reaction was stirred at room temperature for 5 hours. The reaction was evaporated in vacuo to yield a pale yellow oil. The oil was dissolved in MeOH:DMSO (1:1) (1 mL) and purified by MDAP (Method B). The appropriate fraction was evaporated in vacuo to yield the title compound as a pale yellow oil (28 mg).

LCMS (System B): $t_{RET}$=1.04 min; MH$^+$ 461

Intermediate 22: 4-(4-Amino-5-((benzyloxy)methyl)-2-butyl-5H-pyrrolo[3,2-d]pyrimidin-7-yl)but-3-yn-1-ol To a solution of 5-((benzyloxy)methyl)-2-butyl-7-iodo-5H-pyrrolo[3,2-d]pyrimidin-4-amine (3.04 g, 6.97 mmol) in N,N-Dimethylformamide (35 mL) was added bis(triphenylphosphine)palladium(II)dichloride (0.489 g, 0.697 mmol) and copper(I) iodide (0.265 g, 1.394 mmol). The solution was stirred and degassed with Nitrogen for 5 minutes then the reaction mixture placed under a nitrogen atmosphere. A solution of but-3-yn-1-ol (0.733 g, 10.45 mmol) and triethylamine (1.457 mL, 10.45 mmol) in N,N-Dimethylformamide (15 mL) was added dropwise over 5 minutes. The reaction mixture was stirred at ambient temperature for 24 hours. The reaction mixture was concentrated in vacuo at 60° C. and the residue partitioned between 3:1 CHCl$_3$ (250 mL) and water (250 mL). The organic layer was separated and the aqueous layer back extracted with 3:1 CHCl$_3$:IPA (2×100 mL). The combined organic phases were dried (MgSO$_4$), filtered and concentrated in vacuo to give a viscous brown oil (5.34 g). The sample was dissolved in 3:1 CHCl$_3$:IPA and preloaded onto florisil. The sample was purified by chromatography on silica (2×100 g) using agradient of 0-10% methanol-TBME over 40 minutes. The appropriate fractions were combined and evaporated in vacuo to give an orange solid (2.064 g). The solid was triturated with diethyl ether, filtered and dried at 50° C. overnight to give the title compound as a pale brown solid (1.53 g).

LCMS (System B): $t_{RET}$=0.95 min; MH$^+$ 379

Intermediate 23: 4-(4-Amino-5-((benzyloxy)methyl)-2-butyl-5H-pyrrolo[3,2-d]pyrimidin-7-yl)butan-1-ol A solution of 4-(4-amino-5-((benzyloxy)methyl)-2-butyl-5H-pyrrolo[3,2-d]pyrimidin-7-yl)but-3-yn-1-ol (948 mg, 2.505 mmol) in ethyl acetate (50 mL) and ethanol (50 mL) was hydrogenated using the H-cube (settings: 25° C., Full H$_2$, 1 mL/min flow rate) and 10% Pd/C CatCart 70 as the catalyst. The reaction mixture was concentrated in vacuo at 60° C. to give the title compound as a viscous yellow oil which crystallised on standing (884 mg).

LCMS (System B): $t_{RET}$=0.98 min; MH$^+$ 383

Intermediate 24: 4-(4-Amino-5-((benzyloxy)methyl)-2-butyl-5H-pyrrolo[3,2-d]pyrimidin-7-yl)butanal A mixture of 4-(4-amino-5-((benzyloxy)methyl)-2-butyl-5H-pyrrolo[3,2-d]pyrimidin-7-yl)butan-1-ol (884 mg, 2.311 mmol), N-methylmorpholine N-Oxide (420 mg, 3.59 mmol), powdered 4 Å molecular sieves and tetrapropylammonium perruthenate (58 mg, 0.165 mmol) was placed under nitrogen and a mixture of anhydrous dichloromethane (27 mL) and anhydrous acetonitrile (3 mL) added. The reaction mixture was stirred at ambient temperature for 2 hours, Additional N-methylmorpholine N-Oxide (390 mg, 3.33 mmol) and tetrapropylammonium perruthenate (38 mg, 0.108 mmol) in anhydrous DCM (5 mL) was added and the reaction mixture stirred at ambient temperature for a further 2 hours. Additional N-methylmorpholine N-Oxide (130 mg, 1.11 mmol) and tetrapropylammonium perruthenate (100 mg, 0.284 mmol) were added and the reaction mixture stirred at ambient temperature for a further 30 mins, The reaction mixture was filtered through Celite and the cake washed with DCM three times. The reaction solvent was removed in vacuo and the residue dissolved in DCM and passed through Celite a second time. The cake was washed with DCM three times and the solvent removed in vacuo to give a black gum. The sample was dissolved in dichloromethane and purified by chromatography on on silica (100 g) using a gradient of 0-25% methanol-dichloromethane over 40 mins. The appropriate fractions were combined and evaporated in vacuo to give an orange gum with a black tinge. The sample was dissolved in dichloromethane and purified by chromatography on on silica (100 g) using a gradient of 0-25% methanol-dichloromethane over 80 mins. The appropriate fractions were combined and evaporated in vacuo to give the title compound as a pale yellow gum (268 mg).

LCMS (System B): $t_{RET}$=1.08 min; MH$^+$ 381

Intermediate 25: tert-Butyl 4-(4-(4-amino-5-((benzyloxy)methyl)-2-butyl-5H-pyrrolo[3,2-d]pyrimidin-7-yl)butyl)piperazine-1-carboxylate A suspension of 4-(4-amino-5-((benzyloxy)methyl)-2-butyl-5H-pyrrolo[3,2-d]pyrimidin-7-yl)butanal (268 mg, 0.704 mmol) and 4 Å molecular sieves in anhydrous dichloromethane (20 mL) was placed under nitrogen and tert-butyl piperazine-1-carboxylate (262 mg, 1.409 mmol) added. The reaction mixture was stirred at ambient temperature for 1 min then sodium triacetoxyborohydride (299 mg, 1.409 mmol) added and the reaction stirred for a further 30 min, Additional 4 Å molecular sieves were added and the reaction mixture stirred at ambient temperature for an additional 16.5 hours, The reaction mixture was filtered through celite and the cake washed with DCM. The solvent was removed in vacuo to give a viscous yellow oil. The oil was redissolved in DCM (50 mL). The organic layer was washed with saturated sodium hydrogen carbonate solution (50 mL), the layers separated and the aqueous layer back-extracted with DCM (2×25 mL). The combined organic phases were dried through a hydrophobic frit and concentrated in vacuo to give a yellow gum (488 mg). The sample was dissolved in dichloromethane and purified by chromatography on a silica cartridge (100 g) using a 0-10% MeOH:TBME gradient over 40 mins. The appropriate fractions were combined and evaporated in vacuo to give the title compound as a pale yellow gum (338 mg).

LCMS (System B): $t_{RET}$=1.31 min; MH$^+$ 551

Intermediate 26: 5-((Benzyloxy)methyl)-2-butyl-7-(4-piperazin-1-yl)butyl)-5H-pyrrolo[3,2-d]pyrimidin-4-amine tert-Butyl 4-(4-(4-amino-5-((benzyloxy)methyl)-2-butyl-5H-pyrrolo[3,2-d]pyrimidin-7-yl)butyl)piperazine-1-carboxylate (338 mg, 0.614 mmol) was dissolved in 1,4-dioxane (3 mL) and then HCL (4M solution in dioxane) (2 mL, 8.00 mmol) was added slowly. The reaction vessel was sealed and the reaction mixture was stirred at ambient temperature for 15 h during which time a yellow precipitate formed. The reaction mixture was concentrated in vacuo at 55° C. and triturated with diethyl ether to give a yellow gum. The gum was redissolved in methanol and azeotroped with diethyl ether to give the title compound as sticky yellow solid (298 mg).

LCMS (System B): $t_{RET}$=1.03 min; MH$^+$ 451

Intermediate 27: 5-((Benzyloxy)methyl)-2-butyl-7-(4-(4-isopropylpiperazin-1-yl)butyl)-5H-pyrrolo[3,2-d]pyrimidin-4-amine To a stirred suspension of 5-((benzyloxy)methyl)-2-butyl-7-(4-(piperazin-1-yl)butyl)-5H-1-pyrrolo[3,2-d]pyrimidin-4-amine hydrochloride (227 mg, 0.466 mmol), triethylamine (0.071 mL, 0.513 mmol) and 4 Å mol sieves in anhydrous dichloromethane (15 mL) was added acetone (0.05 mL, 0.681 mmol) followed by sodium triacetoxyborohydride (198 mg, 0.932 mmol). The reaction was stirred at ambient temperature for 1.5 h. To the reaction was added further acetone (0.05 mL, 0.681 mmol) and further triethylamine (0.035 mL, 0.256 mmol) and the reaction was stirred at 40° C. for 1 h. The reaction was stirred for a further 45 min before addition of further acetone (0.05 mL, 0.681 mmol) and further sodium triacetoxyborohydride (100 mg, 0.46 mmol) and stirring at 40° C. continued for 16 h. To the reaction was added further acetone (0.05 mL, 0.681 mmol) and further sodium triacetoxyborohydride (100 mg, 0.46 mmol) and stirring at 40° C. continued for 2 h. The reaction mixture was diluted with DCM (35 mL) and filtered through a pad of celite. The filter cake was washed with DCM (10 mL), the combined filtrates were washed with saturated aqueous sodium bicarbonate (50 mL). The organic layer was dried using a hydrophobic frit and concentrated in vacuo. The sample was dissolved in dichloromethane and purified by chromatography on a aminopropyl functionalised silica cartridge (20 g) using a gradient of 0-100% ethyl acetate-cyclohexane over 40 minutes. The appropriate fractions were combined and evaporated in vacuo to give the title compound as a colourless gum (57 mg).

LCMS (System B): $t_{RET}$=1.14 min; MH$^+$ 493

Example Preparation

Example 1

2-Butyl-7-(5-(piperazin-1-yl)pentyl)-5H-pyrrolo[3,2-d]pyrimidin-4-amine

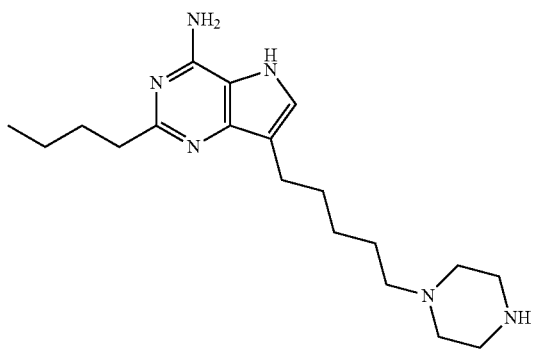 [SMILES: CCCCc1nc(N)c2[nH]cc(CCCCCN3CCNCC3)c2n1]

tert-Butyl 4-(5-(4-amino-5-((benzyloxy)methyl)-2-butyl-5H-pyrrolo[3,2-d]pyrimidin-7-yl)pent-4-yn-1-yl)piperazine-1-carboxylate (80 mg, 0.143 mmol) in ethanol (15 mL) was passed through the H-cube (settings: 45° C., full hydrogen, 1 mL/min flow rate and 10% palladium on carbon CatCart30 as the catalyst). The solution was passed through the H-cube again (settings: 45° C., full hydrogen, 1 mL/min flow rate). The solution was evaporated in vacuo to yield a white solid. The solid was dissolved in MeOH:DMSO (1:1) (1 mL) and purified by MDAP (Method B). Appropriate fractions were combined and evaporated in vacuo to yield a white solid (37 mg). The solid was dissolved in anhydrous methanol (2.5 mL) and 4M hydrogen chloride in 1,4-dioxane (0.5 mL 2 mmol) and stirred at room temperature for 17 hours. The reaction was evaporated to dryness under a stream of nitrogen to yield a yellow oil. The oil was dissolved in MeOH:DMSO (1:1) (1 mL) and purified by MDAP (Method B). Appropriate fractions were combined and evaporated in-vacuo to yield the title compound as a colourless oil (26 mg). LCMS (System B): $t_{RET}$=0.80 min; MH$^+$ 345

Example 2

2-Butyl-7-(5-(4-isopropylpiperazin-1-yl)pentyl)-5H-pyrrolo[3,2-d]pyrimidin-4-amine

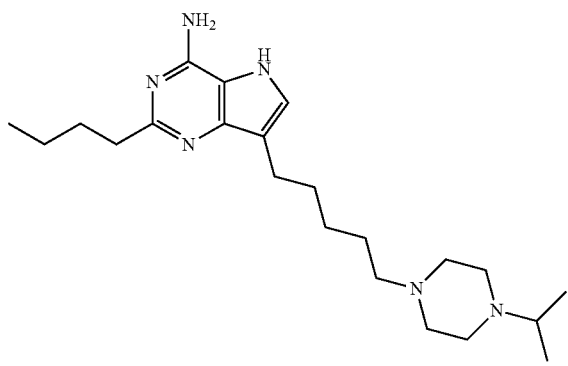 [SMILES: CCCCc1nc(N)c2[nH]cc(CCCCCN3CCN(C(C)C)CC3)c2n1]

5-((Benzyloxy)methyl)-2-butyl-7-(5-(4-isopropylpiperazin-1-yl)pent-1-yn-1-yl)-5H-pyrrolo[3,2-d]pyrimidin-4-amine (77 mg, 0.153 mmol) in ethanol (20 mL) was passed through the H-cube (settings: 45° C., full hydrogen, 1 mL/min flow rate and 10% palladium on carbon CatCart30 as the catalyst). A new 10% palladium on carbon CatCart30 cartridge was inserted into the H-cube and the solution was again passed through the H-cube (settings: 45° C., full hydrogen, 1 mL/min flow rate). The solution was evaporated in-vacuo to yield a white solid. The solid was dissolved in MeOH:DMSO (1:1) (1 mL) and purified by MDAP (Method B). the appropriate fraction was evaporated in-vacuo to yield the title compound as a white solid (21 mg).
LCMS (System B): $t_{RET}$=0.90 min; MH$^+$ 387

Example 3

2-Butyl-7-(5-(4-isopropylpiperazin-1-yl)pentyl)-6-methyl-5H-pyrrolo[3,2-d]pyrimidin-4-amine

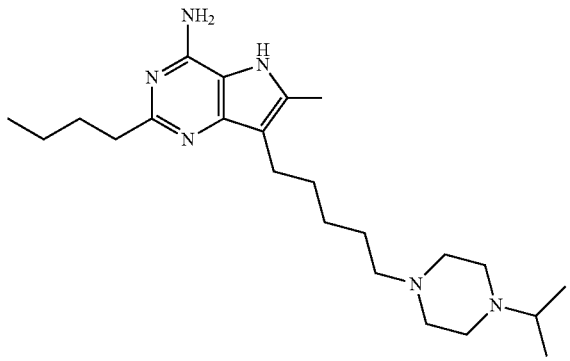 [SMILES: CCCCc1nc(N)c2[nH]c(C)c(CCCCCN3CCN(C(C)C)CC3)c2n1]

A solution of 5-((benzyloxy)methyl)-2-butyl-7-(5-(4-isopropylpiperazin-1-yl)pent-1-yn-1-yl)-6-methyl-5H-pyrrolo[3,2-d]pyrimidin-4-amine (61 mg, 0.118 mmol) in methanol (15 mL) was passed through the H-cube (settings: 40° C., full hydrogen, 1 mL/min flow rate and 10% palladium on carbon CatCart30 as the catalyst) three times. The solution was evaporated in-vacuo to yield 29 mg of pale yellow solid. The crude product was dissolved in 1 mL of 50:50 DMSO/MeOH and purified by MDAP (Method B). Fractions which contained product were concentrated to give the title compound as a white solid (14 mg).
LCMS (System B): $t_{RET}$=0.93 min; MH$^+$ 401

Example 4

2-Butyl-7-(5-(4-ethylpiperazin-1-yl)pentyl)-6-methyl-5H-pyrrolo[3,2-d]pyrimidin-4-amine

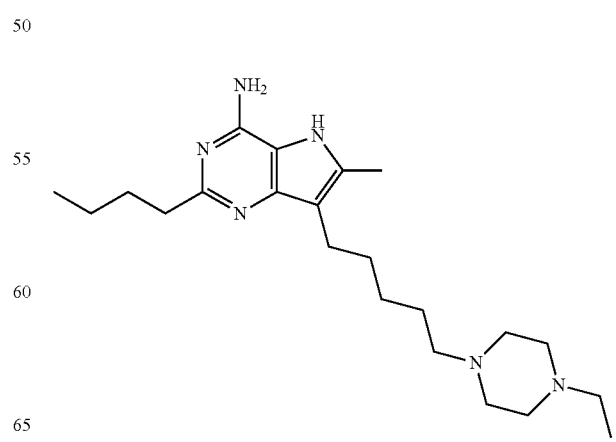

Prepared similarly to Example 3 from 5-((benzyloxy)methyl)-2-butyl-7-(5-(4-ethyl piperazin-1-yl)pent-1-yn-1-yl)-6-methyl-5H-pyrrolo[3,2-d]pyrimidin-4-amine.

LCMS (System B): $t_{RET}$=0.91 min; MH$^+$ 387

Example 5

2-Butyl-7-(3-(piperazin-1-yl)propyl)-5H-pyrrolo[3,2-d]pyrimidin-4-amine

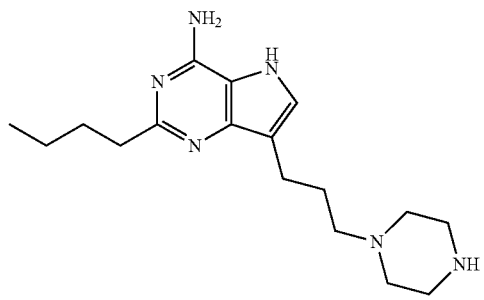 [SMILES: CCCCc1nc(N)c2[nH]cc(CCCN3CCNCC3)c2n1]

Prepared similarly to Example 1 from 5-((benzyloxy)methyl)-2-butyl-7-(5-(4-ethylpiperazin-1-yl)pent-1-yn-1-yl)-6-methyl-5H-pyrrolo[3,2-d]pyrimidin-4-amine.

LCMS (System B): $t_{RET}$=0.68 min; MH$^+$ 317

Example 6

2-Butyl-7-(3-(4-ethylpiperazin-1-yl)propyl)-5H-pyrrolo[3,2-d]pyrimidin-4-amine

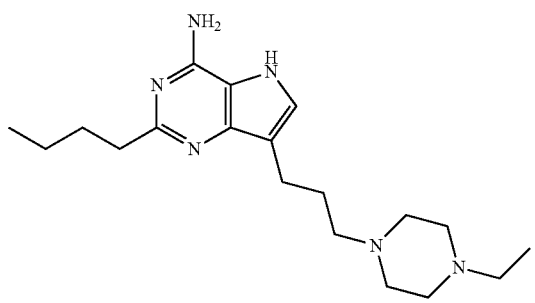 [SMILES: CCCCc1nc(N)c2[nH]cc(CCCN3CCN(CC)CC3)c2n1]

Prepared similarly to Example 1 from 5-((benzyloxy)methyl)-2-butyl-7-(3-(4-ethylpiperazin-1-yl)prop-1-yn-1-yl)-5H-pyrrolo[3,2-d]pyrimidin-4-amine.

LCMS (System B): $t_{RET}$=0.72 min; MH$^+$ 345

Example 7

2-Butyl-7-(4-(4-isopropylpiperazin-1-ylbutyl)-5H-pyrrolo[3,2-d]pyrimidin-4-amine

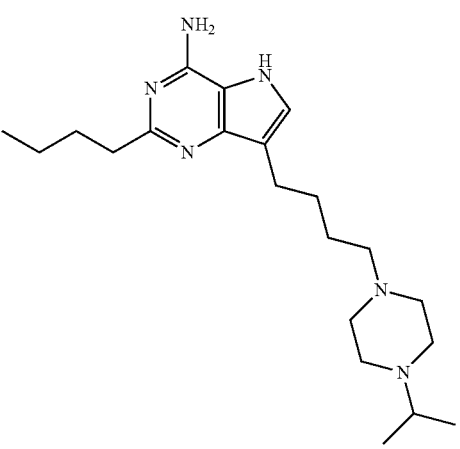 [SMILES: CCCCc1nc(N)c2[nH]cc(CCCCN3CCN(C(C)C)CC3)c2n1]

Prepared similarly to Example 3 from 5-((benzyloxy)methyl)-2-butyl-7-(4-(4-isopropylpiperazin-1-yl)butyl)-5H-pyrrolo[3,2-d]pyrimidin-4-amine LCMS (System B): $t_{RET}$=0.85 min; MH$^+$ 373

Biological Evaluation

Compounds of the invention were tested for in vitro biological activity in accordance with the following assay.
Assay for the Induction of Interferon-α and TNF-α Using Fresh Human Whole Blood (WB)
Compound Preparation Compounds were prepared at 100× required concentration in DMSO in flat-bottom microtitre plates at a volume of 1.5 μL. Columns 1-10 contained a 1 in 4 serial dilution of the test compound. Included on each plate was a serial dilution of the TLR7/8 agonist resiquimod as a standard and Column 11 contained 1.5 μl of 200 μM resiquimod (giving a 2 μM final concentration, used to define the approximate maximal response to resiquimod). Each compound was assayed in duplicate for each donor.
Incubation and Assays for Interferon-α and TNF-α

Blood samples from three human donors were collected into sodium heparin (10 U/ml). 150 μl of whole Blood was dispensed into Col 1 to 11 of assay plates containing 1.5 μl of test compound or standard in DMSO. Plates were placed in an incubator overnight (37° C., 95% air, 5% $CO_2$). Following the overnight incubation, plates were removed from the incubator & mixed on an orbital shaker for approximately 1 minute. 100 μl of 0.9% saline was added to each well and the plates mixed again on an orbital shaker. Plates were then centrifuged (2500 rpm, 10 mins), after which a sample of plasma was removed using a Biomek FX and assayed for both IFN-α and TNF-α using the MSD (Mesoscale Discovery) electrochemiluminescence assay platform. The IFN-α assay was carried out similarly to that described above. The TNF-α assay was carried out as per kit instructions (Cat No K111BHB).

Cytokine released was expressed as a percentage of the 2 μM resiquimod control (column 11). This percentage was plotted against compound concentration and the $pEC_{50}$ for the response determined by non-linear least squares curve fitting. For the IFN-α responses, generally a 4 parameter logistic model was selected. For the TNF-α responses where a clear maximum response was obtained (i.e. a well defined plateau in the response was observed) then a 4 parameter model was generally used. If the upper asymptote of the curve wasn't well defined then the curve fitting was generally constrained to a maximal response of 100% (i.e. to the response to 2 μM resiquimod) or to the response of the highest concentration tested if this was greater than the resiquimod response. Some curves were bell shaped for one or both cytokines and the cytokine data on the down slope of the bell shaped response (i.e. concentrations above those giving the maximal response) were generally excluded from the fit, usually with the exception of the concentration immediately above the peak response. Curve fitting thus concentrated on the up slope of the dose response curve.

RESULTS

Examples 1 to 7 had a mean $pEC_{50}$ for IFN-$\dot{\alpha}$ of ≥5.8.
Examples 1 to 7 had a mean $pEC_{50}$ for TNF-α of ≤5.3.

What is claimed is:
1. A compound of formula (I), or a salt thereof:

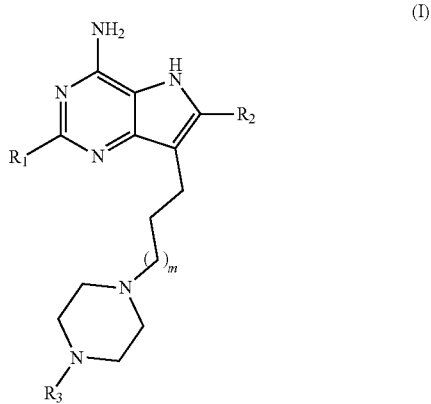

(I)

wherein:
$R_1$ is n-$C_{3-6}$alkyl;
$R_2$ is hydrogen or methyl;
$R_3$ is hydrogen or $C_{1-6}$alkyl;
m is an integer having a value of 1 to 4.

2. The compound or salt thereof according to claim 1 wherein $R_1$ is n-butyl.
3. The compound or salt thereof according to claim 1, wherein $R_2$ is hydrogen.
4. The compound or salt thereof according to claim 1 wherein $R_2$ is methyl.
5. The compound or salt thereof according to claim 1 wherein m is an integer having a value of 1, 2, 3 or 4.
6. The compound or salt thereof according to claim 1 wherein m is an integer having a value of 1 or 3.
7. The compound or salt thereof according to claim 1 wherein $R_3$ is isopropyl or ethyl.
8. The compound or salt thereof according to claim 1 selected from the group consisting of:
  2-Butyl-7-(5-(piperazin-1-yl)pentyl)-5H-pyrrolo[3,2-d]pyrimidin-4-amine;
  2-Butyl-7-(5-(4-isopropylpiperazin-1-yl)pentyl)-5H-pyrrolo[3,2-d]pyrimidin-4-amine;
  2-Butyl-7-(5-(4-isopropylpiperazin-1-yl)pentyl)-6-methyl-5H-pyrrolo[3,2-d]pyrimidin-4-amine;
  2-Butyl-7-(5-(4-ethylpiperazin-1-yl)pentyl)-6-methyl-5H-pyrrolo[3,2-d]pyrimidin-4-amine;
  2-Butyl-7-(3-(piperazin-1-yl)propyl)-5H-pyrrolo[3,2-d]pyrimidin-4-amine;
  2-Butyl-7-(3-(4-ethylpiperazin-1-yl)propyl)-5H-pyrrolo[3,2-d]pyrimidin-4-amine; and
  2-Butyl-7-(4-(4-isopropylpiperazin-1-yl)butyl)-5H-pyrrolo[3,2-d]pyrimidin-4-amine.
9. The compound according to claim 1 which is in the form of a pharmaceutically acceptable salt.
10. The compound according to claim 1 which is in the form of a free base.
11. A pharmaceutical composition comprising a compound or salt thereof as defined in claim 1 and one or more pharmaceutically acceptable excipients.
12. A vaccine composition comprising a compound or salt thereof as defined in claim 1, and an antigen or antigen composition.
13. A method of treatment of allergic rhinitis, which method comprises administering to a human subject in need thereof, a therapeutically effective amount of a compound as defined in claim 1, or a pharmaceutically acceptable salt thereof.
14. A method of treatment of asthma, which method comprises administering to a human subject in need thereof, a therapeutically effective amount of a compound as defined in claim 1, or a pharmaceutically acceptable salt thereof.

* * * * *